US011850270B2

(12) United States Patent
Carlin et al.

(10) Patent No.: US 11,850,270 B2
(45) Date of Patent: Dec. 26, 2023

(54) PROBIOTICS AND METHODS OF USE

(71) Applicant: The Biocollective, LLC, Denver, CO (US)

(72) Inventors: Martha Rodgers Carlin, Lonetree, CO (US); Steven Karim Kazemi, Denver, CO (US); Naseer Sangwan, Chicago, IL (US); Raul De Jesus Cano, San Luis Obispo, CA (US)

(73) Assignee: The Biocollective, LLC, Denver, CO (US)

( * ) Notice: Subject to any disclaimer, the term of this patent is extended or adjusted under 35 U.S.C. 154(b) by 175 days.

(21) Appl. No.: 16/770,064

(22) PCT Filed: Dec. 4, 2018

(86) PCT No.: PCT/US2018/063784
§ 371 (c)(1),
(2) Date: Jun. 4, 2020

(87) PCT Pub. No.: WO2019/113023
PCT Pub. Date: Jun. 13, 2019

(65) Prior Publication Data
US 2021/0315948 A1  Oct. 14, 2021

Related U.S. Application Data

(60) Provisional application No. 62/594,201, filed on Dec. 4, 2017.

(51) Int. Cl.
*A61K 35/747* (2015.01)
*A61K 31/7004* (2006.01)

(52) U.S. Cl.
CPC ........ *A61K 35/747* (2013.01); *A61K 31/7004* (2013.01)

(58) Field of Classification Search
CPC .............. A61K 31/7004; A61K 35/741; A61K 35/744; A61K 35/747
See application file for complete search history.

(56) References Cited

FOREIGN PATENT DOCUMENTS

| WO | 2008/073148 A2 | 6/2008 |
| WO | 2009/030040 A1 | 3/2009 |
| WO | 2014/070225 A1 | 5/2014 |
| WO | 2015/095241 A2 | 6/2015 |
| WO | 2016/110585 A1 | 7/2016 |
| WO | 2016/124266 A1 | 8/2016 |
| WO | 2017/059101 A1 | 4/2017 |

OTHER PUBLICATIONS

Owusu-Kwarteng et al., Journal of Food Research, 2013, vol. 2, No. 1, p. 50-58.*
Mandal et al., World J Microbiol Biotechnol, 2009, vol. 25, p. 1837-1847.*
Patra et al., World J Microbiol Biotechnol, 2011, vol. 27, p. 933-939.*
Ortiz et al., Appl Microbiol Biotechnol, 2012, vol. 95, p. 991-999.*
Khochamit et al., Microbiological Research, 2015, vol. 170, p. 36-50.*
Wisselink et al., International Dairy Journal, 2002, vol. 12, p. 151-161.*
International Search Report, dated Apr. 1, 2019, issued in corresponding International Application No. PCT/US18/63784.
Aarnikunnas J. et al.,"The Mannitol Dehydrogenase Gene (mdh) from Leuconostoc Mesenteroides is Distinct From Other Known Bacterial mdh Genes." Appl Microbiol Biotechnol 59, 665-671 (2002).
Balgir P. et al.,"A Preliminary Clinical Evaluation of Probiotics Pediococcus Acidilactici MTCC5101 and Bacillus Coagulans MTCC492 on Young Anemic Women." International Journal of Fermented Foods. Jun. 2014, vol. 3, pp. 45-49.
Maekawa M. et al., "Butyrate and Propionate Production From D-mannitol in the Large Intestine of Pig and Rat." Microbial Ecology in Health and Disease 17:3, 169-176 (2005).
Ortiz M.E. et al., "Global Analysis of Mannitol 2-Dehydrogenase in Lactobacillus reuteri CRL 1101 During Mannitol Production Through Enzymatic. Genetic and Proteomic Approaches." PLoS ONE 12(1): e0169441 (2017).
Sindhu K. et al., "Immune Response and Intestinal Permeability in Children with Acute Gastroenteritis Treated with Lactobacillus rhamnosus GG: A Randomized, Double-Blind, Placebo-Controlled Trial." Clinical Infectious Disease Apr. 15, 2014, vol. 58, pp. 1107-1115.
Yao K. et al., Effect of Probiotics on Glucose and Lipid Metabolism in Type 2 Diabetes Mellitus: A Meta-Analysis of 12 Randomized Controlled Trials. Medical Science Monitor. Jun. 22, 2017, vol. 23, pp. 3044-3053.
Zhang Q. et al., "Effect of Probiotics on Glucose Metabolism in Patients with Type 2 Diabetes Mellitus: A Meta-Analysis of Randomized Controlled Trials." Medicina. Dec. 29, 2015, vol. 52, pp. 28-34.

* cited by examiner

*Primary Examiner* — Kade Ariani
(74) *Attorney, Agent, or Firm* — Kathleen D. Rigaut; Howson & Howson LLP

(57) ABSTRACT

Disclosed are probiotic formulations. The formulations of the present disclosure comprise microorganisms of the species *Pediococcus acidilactici* and *Leuconostoc mesenteroides*. The formulations of the present disclosure can be used to prevent or treat gastrointestinal disease conditions, notably gastrointestinal diseases associated with low gastrointestinal mannitol or infection of the gastrointestinal system by pathogenic organismsC.

19 Claims, 12 Drawing Sheets

PROBIOTICS AND METHODS OF USE

CROSS-REFERENCE TO RELATED APPLICATIONS

This application is a § 371 of International Application No. PCT/US2018/063784, filed Dec. 4, 2018, which claims priority from US Provisional Patent Application 62/594,201 filed Dec. 4, 2017. The entire disclosure of each of the aforesaid applications is incorporated by reference in the present application.

FIELD OF THE DISCLOSURE

The present disclosure relates to novel probiotic formulations and methods of use thereof to prevent or treat disease conditions. The present disclosure further relates to probiotic formulations and methods of use thereof to prevent disease, limit disease conditions, restore lost physiological function, and reduce gastrointestinal infection by modulating gastrointestinal mannitol.

BACKGROUND OF THE DISCLOSURE

The following paragraphs are provided by way of background to the present disclosure. They are not however an admission that anything discussed therein is prior art or part of the knowledge of persons skilled in the art.

Modern environmental and urban conditions expose people to a variety of chemicals that are added to food, air, and water. These chemicals may include antibiotics used to remedy medical conditions or those that are present in foods such as meats and other animal-derived food products. These chemicals may be toxic pesticides or herbicides, heavy metals, chlorine, disinfection byproducts, or other chemicals found in the environment, food, and in drinking water. One result of this exposure to chemicals is that the microbes comprising the human gut microbiome are exposed to selective pressures that favor some microorganisms over others. For example, if a person regularly consumes meats containing antibiotics, the gut microbiome composition will shift so that microbes containing antibiotic-resistant genes represent a larger fraction of the total gut microbiome. Microbes possessing resistance to antibiotics have a competitive advantage in an environment that is commonly exposed to antibiotics and will, over time, come to represent a larger fraction of the gut microbiome community versus their relative abundance in the microbiome of a person who is not exposed to the same antibiotics. Likewise, other environmental exposures to toxins and chemicals will result in similar shifts in the microbiome with the end result being a microbiome that:
  1. shifts significantly with respect to the relative abundance of microorganisms;
  2. loses critical functionality;
  3. has a higher relative abundance of pathogenic organisms; or
  4. provides poor digestion and/or results in poor health.

Probiotics are commercially available products that provide microbes generally believed to be helpful to the microbiome and to seed it with microbes such as lactic acid bacteria which are believed to be beneficial for health. However, the heretofore known probiotics remain ineffective in the treatment of certain disease conditions. There is therefore a need in the art for novel probiotics capable of treating or preventing certain disease conditions, notably disease conditions that initiate in the gastrointestinal system, or are exacerbated by gastrointestinal-related conditions.

SUMMARY OF THE DISCLOSURE

The following paragraphs are intended to introduce the reader to the more detailed description that follows and not to define or limit the claimed subject matter of the present disclosure.

In one broad aspect, the present disclosure relates to probiotic formulations.

In another broad aspect, the present disclosure relates to the treatment or prevention of disease conditions that may occur in the gastrointestinal system, including diseases that may be caused by gastrointestinal infection, including clinical and subclinical infections, or lack of function of the gastrointestinal microbiome.

In another broad aspect, the present disclosure relates to probiotic formulations comprising a mixture of microorganisms capable of modulating gastrointestinal mannitol.

In one aspect, the present disclosure provides, in accordance with the teachings herein, in at least one embodiment, a probiotic formulation comprising a mixture of viable microorganisms of the species *Pediococcus acidilactici* and at least one of *Leuconostoc mesenteroides* and *Lactobacillus reuteri*.

In at least one embodiment, the probiotic formulation can comprise both *Leuconostoc mesenteroides* and *Lactobacillus reuteri*.

In at least one embodiment, the *Leuconostoc mesenteroides* species can be *Leuconostoc mesenteroides* ssp *mesenteroides*.

In at least one embodiment, the probiotic formulation can further comprise one or more viable microorganisms independently selected from at least one, at least two, at least three, at least four, or all five of *Lactobacillus paracasei, Lactobacillus plantarum, Bifidobacterium bifidum, Bifidobacterium longum* and *Bacillus subtilis*.

In at least one embodiment, the probiotic formulation can further comprise one or more viable microorganisms independently selected from at least one, at least two, at least three, at least four, at least five, at least six, at least seven, at least eight, at least nine, at least ten, at least eleven, at least twelve, at least thirteen, at least fourteen, at least fifteen, at least sixteen, or all seventeen of the microbial species from the group consisting of *Leuconostoc pseudornesenteroides, Leuconostoc sanfrancensis, Leuconostoc amelibiosum, Oenococcus oeni, Lactococcus lactic, Lactococcus intermedius, Lactococcus brevis, Lactococcus buchneri, Lactococcus cellobiosus, Lactococcus fermentum, Lactococcus intermedis, Lactococcus citrovorum, Lactococcus mesenteroides* subsp. *dextranicurn, Lactococcus paramesenteroides, Rhodobacter sphaeroides, Pseudomonas fluorescens*, and *Gluconobacter suboxydans*.

In at least one embodiment, the probiotic formulation can further comprise one or more viable microorganisms independently selected from at least one, at least two, at least three, at least four, at least five, at least six, at least seven, at least eight, or all nine of the microbial species from the group consisting of *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei*, and *Bacillus amyloliquefaciens*.

In at least one embodiment, the probiotic formulation can further be dosed to comprise amounts of about 1×10^6 CFU per dose to about 1×10^12 CFU per dose of each of *Pediococcus acidilactici*, and *Leuconostoc mesenteroides*, or *Lactobacillus reuteri*.

In at least one embodiment, the probiotic formulation can further be dosed to comprise a concentration of about 1×10^6 CFU to about 1×10^12 CFU of each of *Lactobacillus paracasei, Lactobacillus plantarum, Bifidobacterium bifidum, Bifidobacterium longum*, and/or *Bacillus subtilis* per dose.

In at least one embodiment, the probiotic formulation can further be dosed to comprise a concentration of about 1×10^6 CFU to about 1×10^12 CFU of each of *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei*, and/or *Bacillus amyloliquefaciens* per dose.

In at least one embodiment, the probiotic formulation can further comprise at least one probiotic formulary ingredient.

In least one embodiment, the formulary ingredient can be a binder, an excipient or a diluent.

In at least one embodiment, the probiotic formulation can further comprise a prebiotic.

In at least one embodiment, the probiotic formulation can further comprise a prebiotic wherein the prebiotic is an oligosaccharide.

In at least one embodiment, the probiotic formulation can further comprise a prebiotic, wherein the prebiotic is an oligosaccharide is selected from the group consisting of fructooligosaccharides, galactooligosaccharides, xylooligosaccharides, isomaltooligosaccharides, human milk oligosaccharides, inulin oligosaccharides, mannan oligosaccharides, pyrodextrin, levan, maltotriose, pectic oligosaccharides, bimuno-galactooligosaccharides, arabinoxylan, and fucoidan.

In at least one embodiment, the probiotic formulation can further comprise a prebiotic wherein the prebiotic comprises from about 10% (w/w) to about 15% (w/w) of the formulation.

In at least one embodiment, the probiotic formulation can further comprise mannitol as a prebiotic.

In at least one embodiment, the probiotic formulation can further comprise D-mannitol as a probiotic.

In at least one embodiment, the probiotic formulation can further comprise D-mannitol as a prebiotic wherein D-mannitol comprises from about 1% (w/w) to about 4% (w/w) of the formulation.

In at least one embodiment, the probiotic formulation can increase the abundance of microbial gastrointestinal genes associated with mannitol production in a subject upon oral administration of the probiotic formulation to the subject.

In at least one embodiment, the probiotic formulation can increase the abundance of microbial gastrointestinal genes associated with mannitol production in a subject upon oral administration of the probiotic formulation to the subject from 10%, or about 10%, to 35%, or about 35%.

In at least one embodiment, the probiotic formulation can increase gastrointestinal mannitol production of a subject upon oral administration of the probiotic formulation to the subject.

In at least one embodiment, the probiotic formulation can increase the abundance of microbial gastrointestinal genes associated with siderophore production in a subject upon oral administration of the probiotic formulation to the subject.

In at least one embodiment, the probiotic formulation can increase the abundance of microbial gastrointestinal genes associated with siderophore production in a subject upon oral administration of the probiotic formulation to the subject from 5%, or about 5%, to 25%, or about 25%.

In at least one embodiment, the probiotic formulation can increase the siderophore content of gastrointestinal microbes of a subject upon oral administration of the probiotic formulation to the subject.

In at least one embodiment, the probiotic formulation can increase the abundance of microbial gastrointestinal genes associated with mannitol and siderophore production in a subject upon oral administration of the probiotic formulation to the subject.

In at least one embodiment, the probiotic formulation can increase gastrointestinal mannitol production, and increase the siderophore production of gastrointestinal microbes of a subject upon oral administration of the probiotic formulation to the subject.

In at least one embodiment, the probiotic formulation can increase the abundance of microbial gastrointestinal genes associated with butyrate production in a subject upon oral administration of the probiotic formulation to the subject.

In at least one embodiment, the probiotic formulation can increase the abundance of microbial gastrointestinal genes associated with butyrate production in a subject upon oral administration of the probiotic formulation to the subject from 10%, or about 10%, to 30%, or about 30%.

In at least one embodiment, the probiotic formulation can increase the butyrate produced by gastrointestinal microbes of a subject upon oral administration of the probiotic formulation to the subject.

In at least one embodiment, the probiotic formulation can decrease the abundance of microbial gastrointestinal genes associated with bacterial resistance in a subject upon oral administration of the probiotic formulation to the subject.

In at least one embodiment, the probiotic formulation can decrease the abundance of microbial gastrointestinal genes associated with bacterial resistance in a subject upon oral administration of the probiotic formulation to the subject from 10%, or about 10%, to 60%, or about 60%.

In at least one embodiment, the probiotic formulation can increase the abundance of microbial gastrointestinal genes associated with bacteriocin production in a subject upon oral administration of the probiotic formulation to the subject.

In at least one embodiment, the probiotic formulation can increase the bacteriocin content produced by gastrointestinal microbes of a subject upon oral administration of the probiotic formulation to the subject.

In at least one embodiment, the probiotic formulation can increase the abundance of microbial gastrointestinal genes associated with glucose utilization in a subject upon oral administration of the probiotic formulation to the subject.

In at least one embodiment, the probiotic formulation can increase the abundance of microbial gastrointestinal genes associated with glucose production in a subject upon oral administration of the probiotic formulation to the subject from 5%, or about 5%, to 15%, or about 15%.

In at least one embodiment, the probiotic formulation can increase the glucose utilization of gastrointestinal microbes of a subject upon oral administration of the probiotic formulation to the subject.

In at least one embodiment, the probiotic formulation can modulate the gastrointestinal pH in such a manner that the gastrointestinal pH is maintained at a physiological pH.

In at least one embodiment, the probiotic formulation can modulate the gastrointestinal pH in such a manner that the gastrointestinal pH is maintained at a pH of from about 6.0 to about 7.5.

In another aspect, the present disclosure provides methods of treatment using a probiotic.

In one aspect, the present disclosure provides, in at least one embodiment, a method of treating a condition characterized by low mannitol production in the gastrointestinal tract by orally administering to a subject in need thereof a therapeutically effective amount of a probiotic formulation comprising a mixture of viable microorganisms capable of increasing gastrointestinal mannitol production, wherein the probiotic comprises a mixture of viable microorganisms of the species *Pediococcus acidilactici* and at least one of *Leuconostoc mesenteroides* and *Lactobacillus reuteri*.

In at least one embodiment, the probiotic formulation can comprise both *Leuconostoc mesenteroides* and *Lactobacillus reuteri*.

In at least one embodiment, the *Leuconostoc mesenteroides* species can be *Leuconostoc mesenteroides* ssp *mesenteroides*.

In at least one embodiment, the probiotic formulation can further comprise one or more viable microorganisms independently selected from at least one, at least two, at least three, at least four, or all five of *Lactobacillus paracasei, Lactobacillus plantarum, Bifidobacterium bifidum Bifidobacterium longum* and *Bacillus subtilis*.

In at least one embodiment, the method can further comprise administering a probiotic formulation including one or more viable microorganisms independently selected from at least one, at least two, at least three, at least four, at least five, at least six, at least seven, at least eight, at least nine, at least ten, at least eleven, at least twelve, at least thirteen, at least fourteen, at least fifteen, at least sixteen, or all seventeen of the microbial species from the group consisting of *Leuconostoc pseudomesenteroides, Leuconostoc sankancensis, Leuconostoc amelibiosum, Oenococcus oeni, Lactococcus lactis, Lactococcus intermedius, Lactococcus brevis, Lactococcus buchneri, Lactococcus cellobiosus, Lactococcus fermentum, Lactococcus intermedis, Lactococcus citrovorum, Lactococcus mesenteroides* subsp. *dextranicurn, Lactococcus paramesenteroides, Rhodobacter sphaeroides, Pseudomonas fluorescens*, and *Gluconobacter suboxydans*.

In at least one embodiment, the method can further comprise administering a probiotic formulation including one or more viable microorganisms independently selected from at least one, at least two, at least three, at least four, at least five, at least six, at least seven, at least eight, or all nine of the microbial species from the group consisting of *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei*, and *Bacillus amyloliquefaciens*.

In at least one embodiment, the probiotic formulation can further be dosed to comprise amounts of about $1\times10^6$ CFU per dose to about $1\times10^{12}$ CFU per dose of each of *Pediococcus acidilactici*, and *Leuconostoc mesenteroides*, or *Lactobacillus reuteri*.

In at least one embodiment, the probiotic formulation can further be dosed to comprise a concentration of about $1\times10^6$ CFU to about $1\times10^{12}$ CFU of each of *Lactobacillus paracasei, Lactobacillus plantarum, Bifidobacterium bifidum, Bifidobacterium longum*, and/or *Bacillus subtilis* per dose.

In at least one embodiment, the probiotic formulation can further be dosed to comprise a concentration of about $1\times10^6$ CFU to about $1\times10^{12}$ CFU of each of *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei*, and/or *Bacillus amyloliquefaciens* per dose.

In at least one embodiment, the method can further comprise administering a probiotic formulation including a prebiotic.

In at least one embodiment, the method can further comprise administering a probiotic formulation including a prebiotic wherein the prebiotic is an oligosaccharide.

In at least one embodiment, the method can further comprise administering a probiotic formulation including a prebiotic wherein the prebiotic is an oligosaccharide selected from the group consisting of fructooligosaccharides, galactooligosaccharides, xylooligosaccharides, isomaltooligosaccharides, human milk oligosaccharides, inulin oligosaccharides, mannan oligosaccharides, pyrodextrin, levan, maltotriose, pectic oligosaccharides, bimuno-galactooligosaccharides, arabinoxylan, and fucoidan.

In at least one embodiment, the method can further comprise administering a probiotic formulation including a prebiotic wherein the prebiotic is D-mannitol.

In at least one embodiment, the method can further comprise administering a probiotic formulation including a prebiotic comprising from about 10% (w/w) to about 15% (w/w) of the formulation.

In at least one embodiment, the method can further comprise administering a probiotic formulation including a prebiotic wherein the prebiotic is D-mannitol and comprising from about 1% (w/w) to about 4% (w/w) of the formulation.

In at least one embodiment, the probiotic formulation can increase the abundance of microbial gastrointestinal genes associated with mannitol production in a subject upon oral administration of the probiotic formulation to the subject.

In at least one embodiment, the probiotic formulation can increase gastrointestinal mannitol production of a subject upon oral administration of the probiotic formulation to the subject.

In at least one embodiment, the probiotic formulation can increase the abundance of microbial gastrointestinal genes associated with siderophore production in a subject upon oral administration of the probiotic formulation to the subject.

In at least one embodiment, the probiotic formulation can increase the siderophore content of gastrointestinal microbes of a subject upon oral administration of the probiotic formulation to the subject.

In at least one embodiment, the probiotic formulation can increase the abundance of microbial gastrointestinal genes associated with mannitol and siderophore production in a subject upon oral administration of the probiotic formulation to the subject.

In at least one embodiment, the probiotic formulation can increase gastrointestinal mannitol production and the siderophore content of gastrointestinal microbes of a subject upon oral administration of the probiotic formulation to the subject.

In at least one embodiment, the probiotic formulation can increase the abundance of microbial gastrointestinal genes associated with butyrate production in a subject upon oral administration of the probiotic formulation to the subject.

In at least one embodiment, the probiotic formulation can increase the butyrate produced by gastrointestinal microbes of a subject upon oral administration of the probiotic formulation to the subject.

In at least one embodiment, the probiotic formulation can decrease the abundance of microbial gastrointestinal genes associated with bacterial resistance of a subject upon oral administration of the probiotic formulation to the subject.

In at least one embodiment, the probiotic formulation can increase the abundance of microbial gastrointestinal genes associated with bacteriocin production in a subject upon oral administration of the probiotic formulation to the subject.

In at least one embodiment, the probiotic formulation can increase the bacteriocin content of gastrointestinal microbes of a subject upon oral administration of the probiotic formulation to the subject.

In at least one embodiment, the probiotic formulation can increase the abundance of microbial gastrointestinal genes associated with glucose utilization in a subject upon oral administration of the probiotic formulation to the subject.

In at least one embodiment, the probiotic formulation can of increase the glucose utilization of gastrointestinal microbes of a subject upon oral administration of the probiotic formulation to the subject.

In at least one embodiment, the probiotic formulation can modulate the gastrointestinal pH in such a manner that the gastrointestinal pH is maintained at a physiological pH.

In another aspect, the present disclosure relates to treating a subject suspected to suffer from low mannitol production in the gastrointestinal tract.

In one aspect, the present disclosure provides, in a at least one embodiment, a method of treating a subject suspected to suffer from low mannitol production in the gastrointestinal tract by:
  (i) analyzing a stool sample obtained from the subject with respect to the abundance of genes associated with gastrointestinal mannitol production to thereby diagnose a low mannitol gastrointestinal condition in the subject; and
  (ii) orally administering to the subject a therapeutically effective amount of a probiotic formulation comprising a mixture of viable microorganisms of the species *Pediococcus acidilactici* and at least one of *Leuconostoc mesenteroides* and *Lactobacillus reuteri*.

In at least one embodiment, the low mannitol gastrointestinal condition can be associated with a pathogenic bacterial infection of the gastrointestinal system.

In at least one embodiment, the probiotic formulation can be any of the probiotic formulations set forth herein.

In at least one embodiment, the present disclosure provides, a method of treating a subject suspected to suffer from low production of mannitol in the gastrointestinal tract by:
  (i) analyzing a urine or blood sample obtained from the subject with respect to the concentration of mannitol to thereby diagnose a low mannitol condition in the subject; and
  (ii) orally administering to the subject a therapeutically effective amount of a probiotic formulation comprising a mixture of viable microorganisms of the species *Pediococcus acidilactici* and at least one of *Leuconostoc mesenteroides* and *Lactobacillus reuteri*.

In at least one embodiment, low mannitol production in the gastrointestinal tract can be a condition associated with a pathogenic bacterial gastrointestinal infection.

In at least one embodiment, the probiotic formulation can be any of the probiotic formulations set forth herein.

In another aspect, the disclosure relates to the prophylactic administration of a probiotic formulation.

In one aspect, the present disclosure provides, in an at least one embodiment, a method of prophylactically administering a therapeutically effective amount of a probiotic formulation comprising a mixture of viable microorganisms of the species *Pediococcus acidilactici* and at least one of *Leuconostoc mesenteroides* and *Lactobacillus reuteri* to a subject in need thereof to thereby maintain the functional pathway of mannitol production in the gastrointestinal tract and maintain siderophore genes in microorganisms.

In at least one embodiment, the probiotic formulation can be any of the probiotic formulations set forth herein.

In another aspect, the present disclosure relates to methods of preparing probiotic formulations.

In one aspect, the present disclosure provides, in at least one embodiment, a method of preparing a probiotic formulation, the method comprising:
  (i) providing a mixture of viable microorganisms of the species *Pediococcus acidilactici* and at least one of *Leuconostoc mesenteroides* and *Lactobacillus reuteri*; and
  (ii) formulating the mixture to form a probiotic formulation.

In at least one embodiment, the mixture of viable microorganisms can be any mixture of microorganisms set forth herein.

In at least one embodiment, the mixture can be formulated by including a probiotic formulation ingredient selected from a diluent, a binder or an excipient in the mixture.

In another aspect, the disclosure relates to uses of probiotic formulations.

In one aspect, the present disclosure provides, in at least one embodiment, a use of a probiotic formulation comprising a mixture of viable microorganisms of the species *Pediococcus acidilactici* and at least one of *Leuconostoc mesenteroides* and *Lactobacillus reuteri* for treating a subject having a condition characterized by low mannitol production in the gastrointestinal tract.

In at least one embodiment, the probiotic can be any of the probiotics set forth herein.

In one aspect, the present disclosure provides, in at least one embodiment, a probiotic formulation comprising a mixture of viable microorganisms of the species *Pediococcus acidilactici* and at least one of *Leuconostoc mesenteroides* and *Lactobacillus reuteri* for use in the treatment of a subject having a condition characterized by low mannitol production in the gastrointestinal tract.

In at least one embodiment, the probiotic can be any of the probiotics set forth herein.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
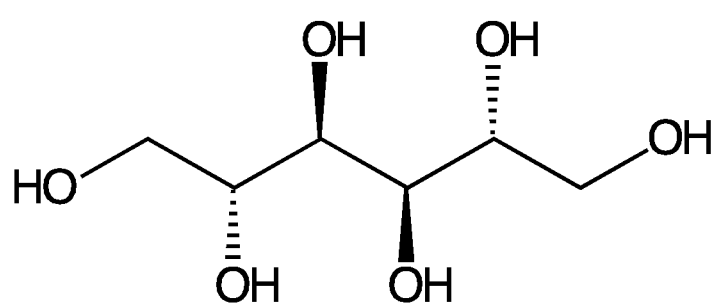
FIG. 1 depicts the chemical structure of D-mannitol.

The figures together with the following detailed description make apparent to those skilled in the art how the disclosure may be implemented in practice.

DETAILED DESCRIPTION OF THE DISCLOSURE

Various compositions, methods or processes will be described below to provide an example of an embodiment of each claimed subject matter. No embodiment described below limits any claimed subject matter and any claimed subject matter may cover processes, compositions or methods that differ from those described below. The claimed subject matter is not limited to compositions, processes or methods having all of the features of any one composition, system or process described below or to features common to multiple or all of the compositions, systems or methods described below. It is possible that a composition, method or process described below is not an embodiment of any claimed subject matter. Any subject matter disclosed in a composition, method or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such as "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either". The term "and/or" is intended to represent an inclusive or. That is "X and/or Y" is intended to mean X or Y or both, for example. As a further example, X, Y, and/or Z is intended to mean X or Y or Z or any combination thereof.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent or patent application was specifically and individually indicated to be incorporated by reference in its entirety.

Terms and Definitions

The term "low-mannitol gastrointestinal condition" or "low mannitol production", as used herein relates to a condition in a subject characterized by a low relative abundance of genes associated with gastrointestinal mannitol production versus the relative abundance of the same genes in a healthy cohort and therefore, low concentrations of mannitol in the gastrointestinal tract or blood or urine, including, without limitation, conditions associated with gastrointestinal infection by pathogenic microorganisms. Abnormally low concentrations further include the substantial absence of mannitol in the gastrointestinal system, blood, and urine, as indicated by the determination in gastrointestinal-mannitol, blood-mannitol, or urine-mannitol detection assays, and conditions in which the mannitol concentration is lower than the level measured in a healthy cohort.

The terms "probiotic" and "probiotic preparation", as may be used interchangeably herein, refer to a mixture of microorganisms which when orally administered can provide health benefits to a human or a non-human animal.

The term "prebiotic", as used herein, means an ingredient for optional inclusion in a probiotic formulation capable of inducing growth or activity of microorganisms in the gastrointestinal system.

The term "probiotic formulation", as used herein, refers to a formulation comprising a probiotic preparation formulated together with one or more additional formulary ingredients to obtain a finished formulation suitable for oral delivery to a human or a non-human animal.

The term "mannitol", as used herein, refers to a chemical compound having the structure set forth in FIG. 1.

The term "microbiome" refers to the community of microbial species present in a gastrointestinal system.

Figure 2A:
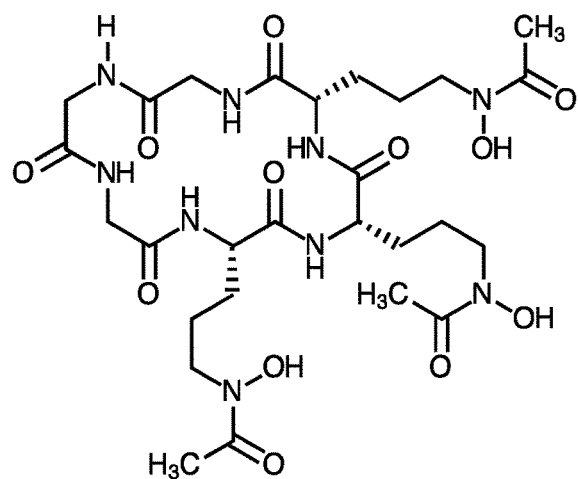
FIGS. 2A-2C depict the chemical structures of example siderophores, notably ferrichrome siderophore (FIG. 2A), enterobactin siderophore (FIG. 2B) and catecholate-iron complex (FIG. 2C).
Figure 2B:
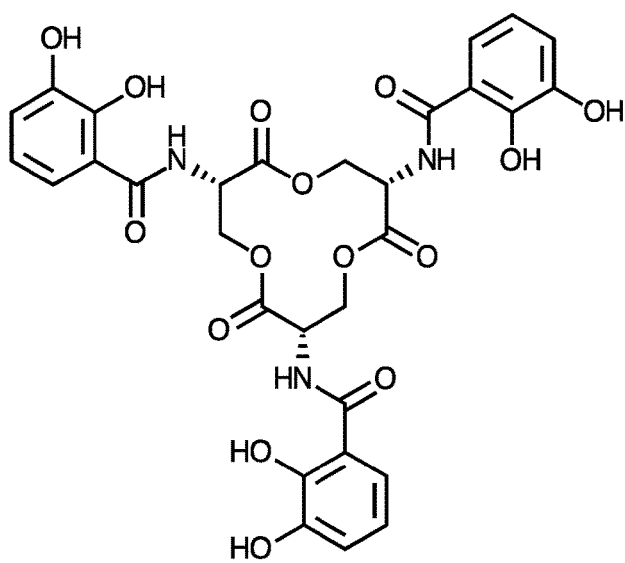
Figure 2C:
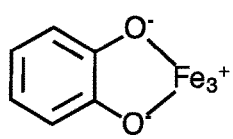

The term "siderophore", as used herein, refers to small molecule high-affinity iron-chelating compounds, including hexadentate and octahedral complexes capable of preferential coordination with $Fe^{3+}$ ions, compared to other abundantly naturally occurring metal ions. Examples of siderophores are illustrated in FIGS. 2A-2C.

The term "subject in need thereof", as used herein, means a subject identified as needing therapy or treatment and can include a human subject for medical purposes, such as for the treatment of an existing disease, disorder, condition, or the prophylactic treatment for preventing the onset of a disease, disorder, or condition, or an animal subject for medical, veterinary purposes, or developmental purposes.

The term "therapeutically effective amount", as used herein, refers to an amount of a formulation sufficient to prevent or bring about treatment of a condition, disorder or a disease, or symptoms thereof, including, without limitation, a gastrointestinal condition, a subclinical or clinical gastrointestinal infection, for example, and further including, suboptimal gastrointestinal mannitol levels, for example, and can fall in relatively wide range that can be determined by routine trials.

Bacterial species are presented herein by Latin names in accordance with the Linnaean taxonomic biological classification system. Accordingly reference is made to microorganisms which can be with identified with reference to certain genus, species, subspecies and strain names. In each instance, non-genetically modified and genetically modified microorganisms are intended to be included.

General Implementation

It is believed that many ailments result from the chronic presence of pathogenic organisms in the gastrointestinal system. These pathogens disrupt the normal function of the gastrointestinal system and can result in bacterial toxin production or inflammation. Communication between the gastrointestinal system and the brain via the vagus nerve can result in a brain that is also under stress from chronic infection. In overview, it has surprisingly been realized that probiotic formulations comprising microorganisms of the species *Pediococcus acidilactici* and at least one of *Leuconostoc mesenteroides* and *Lactobacillus reuteri* can modulate the microbial metabolism across the gastrointestinal system and thereby maintain, form or restore certain metabolic pathways, including metabolic pathways relating to gastrointestinal mannitol production and increase in the abundance of protein coding genes involved in microbial siderophore production and pathways relating to butyrate production. The creation, restoration or maintenance of these pathways is beneficial to human health. The probiotic formulations of the present disclosure may be administered to subjects in need thereof, including subjects diagnosed with suboptimal gastrointestinal mannitol production. Furthermore it has, surprisingly, been found that a probiotic formulation comprising *Pediococcus acidilactici* and at least one of *Leuconostoc mesenteroides* and *Lactobacillus reuteri* can modulate the gastrointestinal pH in such a manner that the gastrointestinal pH remains at physiological levels. Under these conditions, metabolic activity, including the production of mannitol, by the microorganisms can be maintained.

In what follows selected example embodiments are described. Accordingly, the present disclosure provides in one aspect, in at least one embodiment, a probiotic formulation comprising a mixture of viable microorganisms of the species *Pediococcus acidilactici* and at least one of *Leuconostoc mesenteroides* and *Lactobacillus reuteri*. The *Leuconostoc mesenteroides* can include, in one embodiment, *Leuconostoc mesenteroides* ssp *mesenteroides*.

A variety of *Pediococcus acidilactici* strains may be used in accordance herewith including, for example, a *Pediococcus acidilactici* strain PCLL01.

A variety of *Leuconostoc mesenteroides* strains may be used in accordance herewith including, for example, a *Leuconostoc mesenteroides* strain TBCLM001.

A variety of *Lactobacillus reuteri* strains may be used in accordance herewith including, for example, a *Lactobacillus reuteri* strain PCR7.

In one embodiment, the probiotic formulation can further include a viable microorganism independently selected from at least one, at least two, at least three, at least four, or all five of *Lactobacillus paracasei, Lactobacillus plantarum, Bifidobacterium bifidum Bifidobacterium longum* and *Bacillus subtilis*.

In one embodiment, the probiotic formulation can further comprise a viable microorganism independently selected from at least one, at least two, at least three, at least four, at least five, at least six, at least seven, at least eight, at least nine, at least ten, at least eleven, at least twelve, at least thirteen, at least fourteen, at least fifteen, at least sixteen, or all of the microbial species from the group consisting of *Leuconostoc pseudomesenteroides, Leuconostoc sanfrancensis, Leuconostoc amelibiosum, Oenococcus oeni, Lactococcus lactis, Lactococcus intermedius, Lactococcus brevi, Lactococcus buchneri, Lactococcus cellobiosus, Lactococcus fermentum, Lactococcus intermedis, Lactococcus citrovorum, Lactococcus mesenteroides* subsp. *dextranicum, Lactococcus paramesenteroides, Rhodobacter sphaeroides, Pseudomonas fluorescens*, and *Gluconobacter suboxydans*.

In one embodiment, the *Leuconostoc amelibiosum* species is a *Leuconostoc amelibiosum* strain B-742.

In one embodiment, the *Lactococcus intermedius* species is a *Lactococcus intermedius* strain NRRL B-3693.

In one embodiment, the *Lactococcus buchneri* species is a *Lactococcus buchneri* strain B-1860.

In one embodiment, the *Lactococcus cellobioses* species is a *Lactococcus cellobioses* strain B-1840.

In one embodiment, the *Lactococcus citrovorum* species is a *Lactococcus citrovorum* strain B-1147.

In one embodiment, the *Lactococcus mesenteroides* subsp. *dextranicum* species is a *Lactococcus mesenteroides* subsp. *dextranicum* strain B-1120.

In one embodiment, the *Lactococcus paramesenteroides* species is a *Lactococcus paramesenteroides* B-3471 strain.

In one embodiment, the *Lactococcus lactis* species is a strain selected from the group consisting of *Lactococcus lactis* strain F17851, *Lactococcus lactis* strain F110089 ldh mutant, *Lactococcus lactis* strain F19630 double mutant, and *Lactococcus* strain MG1363.

In one embodiment, the probiotic formulation further comprises a mixture of viable microorganisms independently selected from at least one, at least two, at least three, at least four, at least five, at least six, at least seven, or at least eight, of the microbial species from the group consisting of *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei*, and *Bacillus amyloliquefaciens*.

In one embodiment, the probiotic formulation further comprises a mixture of viable microorganisms comprising *Lactobacillus plantarum, Lactobacillus paracasei, Lactobacillus rhamnosus, Bifidobacterium bifidum, Bifidobacterium longum, Bacillus subtilis, Lactobacillus casei, Lactobacillus helveticus*, and *Bacillus amyloliquefaciens*.

In one embodiment, the *Lactobacillus casei* species is a *Lactobacillus casei* W8 strain.

In one embodiment, the *Lactobacillus helveticus* species is a *Lactobacillus helveticus* R0052. Strain.

A substantially pure aliquot of each of the microorganisms of the present disclosure can be obtained from a microorganism culture collection, for example, from the American Type Culture Collection (ATCC) or a similar collection, or from private companies such as BioSource Flavors Inc., Pure Cultures Inc., or Nutraceutix Inc. Upon obtaining the aliquot of a microorganism it can be grown in quantities, as desired, and cultured under appropriate conditions, for example in a liquid growth medium comprising appropriate microbial nutrients, and thereafter the microorganisms can be harvested under conditions ensuring that viable microorganisms are retained from the medium, and the harvested microorganisms can be used to prepare the probiotic formulations of the present disclosure. In embodiments hereof where the probiotic formulation comprises a plurality of microbial species, the species can be co-cultured, or alternatively separately grown and mixed upon harvesting. General growing conditions for growing Lactobacilli, MRS Agar, was developed by researchers deMan, Rogosa and Sharpe, as described in de Man, J. D.; Rogosa, M.; Sharpe, M. E. (1960). "A Medium for the Cultivation of Lactobacilli". J Appl Bact. 23 (130-135)). *Pediococcus acidilactici* and *Leuconostoc mesenteroides* ssp *mesenteroides* and *Lactobacillus reuteri* may all be grown using MRS growth media, or modifications thereof. MRS growth medium can contain, for example:

1.0% peptone
1.0% beef extract
0.4% yeast extract
2.0% glucose
0.5% sodium acetate trihydrate
0.1% polysorbate 80 (also known as Tween 80)
0.2% dipotassium hydrogen phosphate
0.2% triammonium citrate
0.02% magnesium sulfate heptahydrate
0.005% manganese sulfate tetrahydrate
1.0% agar
pH adjusted to 6.2 at 25° C.

In order to prepare the probiotic formulations of the present disclosure, a quantity of *Pediococcus acidilactici* and a quantity of *Leuconostoc mesenteroides* ssp *mesenteroides* or *Lactobacillus reuteri* is obtained and mixed to obtain a probiotic preparation. In one embodiment, *Pediococcus acidilactici* is mixed with *Leuconostoc mesenteroides* ssp *mesenteroides* or *Lactobacillus reuteri* in a concentration sufficient to prepare a probiotic formulation to a final concentration per dose of, for example, from about $1 \times 10^6$ CFU to about $1 \times 10^{12}$ CFU for each species. In this manner, a probiotic preparation can be obtained. The probiotic preparation can then be used to prepare a probiotic formulation. Probiotic formulations as used herein are formulations comprising a probiotic preparation formulated together with one or more additional formulary ingredients. Upon formulation, the probiotic formulations of the present disclosure can be directly used for oral delivery, including in the form of a dietary supplement or medicinal food. Probiotic formulations further also include formulations that can be used as a formulation ingredient for inclusion in a food or a feed. The probiotic formulations of the present disclosure can for example, be incorporated in a dairy product, such as milk, and in particular a fermented dairy product, for example with yogurt ferments, or other food products such as a snack bar, or beverages, such as a fruit or vegetable juice. In further embodiments, the probiotics may be included in a medical food, such as medical foods intended for dietary intervention, for example medical food comprising extensively hydrolyzed casein formula supplemented with probiotic strains e.g. *Lactobacillus rhamnosus*, probiotics containing biscuit, or a milk-based fruit drink containing a probiotic strain, or rectally delivered as a suppository or enema.

Formulary ingredients that can be used to prepare a finished probiotic formulation can vary substantially. In one embodiment, the finished probiotic formulation, in addition to the viable microorganisms can include a formulary ingredient suitable for incorporation in a probiotic formulation selected from a binder, such as a starch, sugar or cellulose, or a derivative thereof; an excipient, such as gelatin, or polyethylene glycol; or a diluent, such as water, or a buffer, for example. Orally dosed formulations, for example, can, in addition to the viable microorganisms comprise, inert compression aids, such as microcrystalline cellulose or oligosaccharide, flow aids, such as a silica gel, or a lubricant of, for example magnesium stearate (vegetable source) or stearic acid (vegetable source). Suppository formulations, for example, either for rectal or vaginal use, can in addition to the probiotics, comprise, for example, cocoa butter, polyethylene glycol, glycerine or gelatine.

In one embodiment, the probiotic formulation can comprise a prebiotic as a formulary ingredient. In one embodiment, the prebiotic can be selected from the group of prebiotics consisting of fructooligosaccharides, P95 NUTRAFLORA® (soluble prebiotic fiber containing a minimum of 95% (dry basis) shortchain fructooligosaccharides), for example, galactooligosaccharides, xylooligosaccharides, isomaltooligosaccharides, human milk oligosaccharides, inulin oligosaccharides, mannan oligosaccharides, pyrodextrin, levan, maltotriose, pectic oligosaccharides, bimuno-galactooligosaccharides, arabinoxylan, and fucoidan.

Formulary ingredients can be contacted with a probiotic preparation and mixed or prepared until a probiotic formulation is obtained. As will be clear to those of skill in the art, formulation conditions will generally be such that viable microorganisms are retained. In particular high temperatures, for example temperatures in excess of 40° C. are avoided.

The probiotic formulations in accordance herewith can vary substantially and can include solid or semisolid formulations, as well as liquid formulations and can further include powders, tablets, such as lozenges or effervescent tablets, pastilles, or capsules.

The amount of viable microorganisms included in a probiotic formulation can vary and can be adjusted and optimized as will be appreciated by those of skill in the art, Such optimization may, for example, be achieved by preparing a series of different doses of a viable microorganism, for example ranging in 1×10^6 CFU to 1×10^12 CFU and testing the different doses, for example, two or more doses selected from about 1×10^6; about 1×10^7 CFU; about 1×10^8 CFU; about 1×10^9 CFU; about 1×10^10 CFU; about 1×10^11 CFU; or about 1×10^12 CFU, with respect to efficacy, for example by administration thereof to a test subject and evaluate, for example, the relative abundance of gastrointestinal genes associated with mannitol production. Upon having identified a desirable dose of a microorganism, it may be selected to prepare further probiotic formulations.

In one embodiment, the probiotic formulation can further be dosed to comprise relative amounts of about 1×10^6 CFU per dose to about 1×10^12 CFU per dose of *Pediococcus acidilactici*, and about 1×10^6 CFU per dose to about 1×10^12 CFU per dose of *Leuconostoc mesenteroides*, or about 1×10^6 CFU per dose to about 1×10^12 CFU per dose of *Lactobacillus reuteri*. Thus, a dose can include, for example, of about 1×10^6; about 1×10^7 CFU; about 1×10^8 CFU; about 1×10^9 CFU; about 1×10^10 CFU; about 1×10^11 CFU; or about 1×10^12 CFU, of each of the aforementioned species. A dose can further include from about 1×10^7 CFU per dose to about 1×10^11 CFU per dose of *Pediococcus acidilactici*, and about 1×10^7 CFU per dose to about 1×10^11 CFU per dose of *Leuconostoc mesenteroides*, or about 1×10^7 CFU per dose to about 1×10^11 CFU per dose of *Lactobacillus reuteri*; or from about 1×10^8 CFU per dose to about 1×10^10 CFU per dose of *Pediococcus acidilactici*, and about 1×10^8 CFU per dose to about 1×10^10 CFU per dose of *Leuconostoc mesenteroides*, or about 1×10^8 CFU per dose to about 1×10^18 CFU per dose of *Lactobacillus reuteri*. Relative dosing of the species may be approximately equal or different. For example, in some formulations, *Pediococcus acidilactici* may be included in a dose to be in excess about 10×, 100×, 1,000× or 10,000× relative to *Leuconostoc mesenteroides* and/or *Lactobacillus reuteri*. In some formulations *Leuconostoc mesenteroides* and/or *Lactobacillus reuteri* may be included in a dose to be in excess about 10×, 100×, 1,000× or 10,000× relative to *Pediococcus acidilactici*.

In one embodiment, the probiotic formulation can further be dosed to comprise a concentration of about 1×10^6 CFU to about 1×10^12 CFU of each of *Lactobacillus paracasei, Lactobacillus plantarum, Bifidobacterium bifidum, Bifidobacterium longum,* and *Bacillus subtilis* per dose. Thus, a dose can include, for example, of about 1×10^6; about 1×10^7 CFU; about 1×10^8 CFU; about 1×10^9 CFU; about 1×10^10 CFU; about 1×10^11 CFU; or about 1×10^12 CFU, of each of the aforementioned species. Relative dosing of species may be approximately equal or different.

In one embodiment, the probiotic formulation can further be dosed to comprise a concentration of about 1×10^6 CFU to about 1×10^12 CFU of each of *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei,* and *Bacillus amyloliquefaciens* per dose. Thus, a dose can include, for example, of about 1×10^6; about 1×10^7 CFU; about 1×10^8 CFU; about 1×10^9 CFU; about 1×10^10 CFU; about 1×10^11 CFU; or about 1×10^12 CFU, of each of the aforementioned species. Relative dosing of the species may be approximately equal or different.

The probiotic formulations of the present disclosure can be administered to subjects in need thereof including humans and non-human animals, for example, cows, pigs, poultry and fish. Administration to humans includes administration by a medical professional and self-administration.

In general, in order to achieve a health benefit, multiple doses of the probiotic formulations are administered, for example daily for a period of at least one week, at least two weeks, at least three weeks, at least six weeks, at least nine weeks, or at least twelve weeks. In one embodiment, the probiotics can be administered for the remaining duration of a subject's life.

In one embodiment, the probiotic formulations of the present disclosure are capable of modulating gastrointestinal mannitol production of a subject upon oral administration of the probiotic formulation to the subject. Thus upon oral administration of the probiotic formulations of the present disclosure the mannitol production pathway can be restored and mannitol levels in the body can be increased.

In one embodiment, the probiotic formulations of the present disclosure are capable of modulating the abundance of microbial genes associated with a metabolic pathway resulting in gastrointestinal mannitol production of a subject upon oral administration of the probiotic formulation to the subject. These genes include the following: mannitol-1-phosphate 5-dehydrogenase (MtlD), mannitol dehydrogenase (MDH), and D-arabinitol 4-dehydrogenase genes (Otte S., Lengeler J. W. The mtl genes and the mannitol-1 phosphate dehydrogenase from Klebsiella pneumoniae KAY2026 FEMS Microbiol Lett. 2001 Jan. 15; 194(2):221-7; Ortiz M. E., Bleckwedel J., Fadda S., Picariello G., Hebert E. M., Raya R. R., Mozzi F. Global analysis of mannitol 2-dehydrogenase in *Lactobacillus reuteri* CRL 1101 during mannitol production through enzymatic, genetic and proteomic approaches. PLoS One. 2017 Jan. 6; 12(1):e0169441. doi: 10.1371/journal.pone.0169441. ecollection 2017; and Ortiz M. E., Raya R. R., Mozzi F. Efficient mannitol production by wild-type *Lactobacillus reuteri* CRL 1101 is attained at constant pH using a simplified culture medium. Appl. Microbiol. Biotechnol. 2015 oct; 99(20):8717-29. doi: 10.1007/s00253-015-6730-y. epub 2015 Jun. 18).

Thus upon oral administration of the probiotic formulations of the present disclosure, the abundance of microbial gastrointestinal genes associated with the mannitol production metabolic pathway can be increased.

In one embodiment, upon oral administration of formulations according to the present disclosure to a subject, the abundance of microbial genes associated with mannitol production can increase about, or at least about, 10%, about, or at least about, 15%, about, or at least about, 20%, about, or at least about, 25%, about, or at least about, 30%, about, or at least about 35%.

In one embodiment, the abundance of microbial genes associated with mannitol production can increase from 10%, or about 10%, to 35%, or about 35%.

A variety of physiological improvements can be observed in subjects to whom the probiotic formulations have been administered. They include improved mitochondrial function, improved folic acid/vitamin B production, decreased blood glucose levels, decreased insulin production, decreased presence of pathogenic microorganisms, decreased antimicrobial resistance, increased production of bacteriocins, increased production of lantibiotics, increased production of short-chain fatty acids, including butyrate, decreased susceptibility to inflammation, and a stronger immune response.

At least a portion of the gastrointestinal mannitol (produced via microbial anaerobic carbohydrate metabolism) can affect the microglia-mediated immune response or change the alpha-synuclein aggregation levels which can thereafter influence the blood-brain barrier (BBB). Thus beneficial effects associated with mannitol can be achieved in the gastrointestinal system, and elsewhere. Further beneficial effects of increases in gastrointestinal mannitol production include the following: gastrointestinal mannitol can function as a diuretic and can increase water and sodium excretion throughout the body, and decreased extracellular fluid volume, and minimize constipation. Furthermore mannitol can have a positive effect on migraine headaches. Mannitol can also facilitate the transportation of pharmaceutical agents, and is capable of opening the blood-brain barrier by temporarily shrinking the endothelial cells and simultaneously shrinking the junctions between the endothelial cells. Mannitol also can act as an antioxidant by up-regulating the level of catalase by increasing oxygen free-radical levels and lipid peroxide. Furthermore mannitol can effect degradation of protein plaques, including alpha-synuclein protein plaques associated with Lewy bodies present in brain tissue of individuals diagnosed with neurological conditions, including, Parkinson's Disease and Alzheimer's Disease. For these and other beneficial health effects of mannitol, see: Fubini, P. (ed). Mannitol Chemistry, Uses and Potential Side Effects. Nova Science Publishers, New York, NY. 2013. Thus it will be clear that there are a variety of health benefits associated with an increase in production of mannitol in the gastrointestinal tract.

In one aspect the present disclosure can include the in vivo production of mannitol via microbiological means. Without wishing to be bound by theory, the microorganisms in the probiotic formulations of the present disclosure may utilize monosaccharides and disaccharides such as fructose, glucose, maltose, mannose, and galactose, as precursor compounds to form mannitol. As mannitol levels in the body increase, an equilibrium can be achieved between mannitol and fructose. Therefore, mannitol concentrations can be expected to stabilize as fructose levels rise. The present disclosure advantageously utilizes in vivo transformation of these monosaccharides and disaccharides to form mannitol as opposed to directly administering mannitol, for example, in drink form or intravenously. This distinction can result in the reduction of total blood glucose, and in increased mannitol levels. The result can be an increase in mannitol in the gastrointestinal tract, blood, and urine.

In one embodiment, the probiotic formulations of the present disclosure can further modulate the gastrointestinal siderophore content of gastrointestinal microorganisms of a subject upon administration of the probiotic formulation to the subject. In one embodiment, the gastrointestinal siderophore content of the of gastrointestinal microorganisms of the microbiome of a subject may increase upon administration of the probiotic formulation to the subject. In one embodiment, the gastrointestinal siderophore content of the gastrointestinal microorganisms of the microbiome of a subject may increase, relative to the gastrointestinal siderophore content of a pathogenic portion of gastrointestinal microorganisms of the microbiome of a subject, upon administration of the probiotic formulation to the subject. In one embodiment, the probiotic formulations of the present disclosure can modulate the abundance of microbial genes associated with a metabolic pathway resulting in siderophore production of a subject upon oral administration of the probiotic formulation to the subject. The modulation can be an increase in siderophore genes observed in non-pathogenic microorganisms. These genes include those that are active in the iron siderophore sensor and receptor system including siderophore achromobactin, siderophore aerobactin, siderophore desferrioxamine E, and siderophore enterobactin.

In one embodiment, the siderophores can be a catecholate, a hydroxamate, or a carboxylate. Examples of bacterial siderophores include ferrichrome siderophore, enterobactin siderophore and catecholate-iron complex (see: FIGS. 2A-2C).

Without wishing to be bound by theory, an increase in gastrointestinal siderophore production may be causatively linked to an increase in mannitol production. It is believed that an increase in gastrointestinal siderophore production can be beneficial to a subject, since siderophores are involved in the acquisition of elemental iron, a microbial nutrient. It is further believed that in certain low gastrointestinal siderophore environments, pathological microorganisms can proliferate at the expense of non-pathogenic microorganisms, and thereby contribute negatively to the of health the microbiome of a subject.

In one embodiment, upon oral administration of formulations according to the present disclosure to a subject, the abundance of microbial gastrointestinal genes associated with siderophore production can increase about or at least about 5%, about or at least about 5%, about, or at least about 10%, about, or at least about 15%, about, or at least about 20%, about, or at least about 25%.

In one embodiment, the abundance of microbial gastrointestinal genes associated with mannitol production can increase from 5%, or about 5%, to 25%, or about 25%.

In one embodiment, the probiotic formulation can increase the butyrate content by gastrointestinal microbes of a subject upon oral administration of the probiotic formulation to the subject. Gastrointestinal butyrate production can be beneficial for a variety of reasons, Butyrate is known to act as anti-inflammatory agent, to promote transepithelial fluid transport, ameliorate mucosal inflammation, reinforce the ephithelial defense barrier and modulate visceral sensitivity and intestinal motility (Canani, R. B., et al. 2011. Potential beneficial effects of butyrate in intestinal and extraintestinal diseases. World Journal of Gastroenterology. 17(12) 1519-1528).

In one embodiment, the probiotic formulation can increase the abundance of microbial gastrointestinal genes associated with butyrate production in a subject upon oral administration of the probiotic formulation to the subject.

In one embodiment, the probiotic formulation can increase the abundance of microbial gastrointestinal genes associated with butyrate production in a subject upon oral administration of the probiotic formulation to the subject from 10%, or about 10%, to 30%, or about 30%.

In one embodiment, the probiotic formulation can increase the bacteriocin content of gastrointestinal microbes of a subject upon oral administration of the probiotic formulation to the subject. Example bacteriocins, that can be increased include pediocin A and enterobactin.

In one embodiment, the probiotic formulation can decrease the abundance of microbial gastrointestinal genes associated with bacterial resistance in a subject upon oral administration of the probiotic formulation to the subject.

In one embodiment, the probiotic formulation can decrease the abundance of microbial gastrointestinal genes associated with bacterial resistance in a subject upon oral administration of the probiotic formulation to the subject from 10%, or about 10%, to 60%, or about 60%.

In one embodiment, the probiotic formulation can increase the abundance of microbial gastrointestinal genes associated with glucose utilization in a subject upon oral administration of the probiotic formulation to the subject.

In one embodiment, the probiotic formulation can increase the abundance of microbial gastrointestinal genes associated with glucose production in a subject upon oral administration of the probiotic formulation to the subject from 5%, or about 5%, to 15%, or about 15%.

In one embodiment, the probiotic formulation can increase the glucose utilization of gastrointestinal microbes of a subject upon oral administration of the probiotic formulation to the subject.

In one embodiment, the probiotic formulation can modulate the gastrointestinal pH such that the gastrointestinal pH is maintained at a physiological pH, for example from a pH of about 6.0 to about 7.5. It is noted, in particular, that the administration of the probiotic of the present disclosure does not result in a lowering of the gastrointestinal pH into the strongly acidic range, below pH 5.0 or 4.0, for example. This can permit the ongoing growth and metabolic activity of microorganisms, including the production of mannitol by *Leuconostoc mesenteroides* and/or *Lactobacillus reuteri*, species which at a lower pH would no longer be metabolically active and stop the production of mannitol.

In another aspect, the present disclosure provides, in at least one embodiment, a method of treating a low mannitol gastrointestinal condition in a subject in need thereof by orally administering to the subject a therapeutically effective amount of a probiotic formulation comprising a mixture of viable microorganisms capable of increasing gastrointestinal mannitol production.

Conditions or symptoms associated with low mannitol production in the gastrointestinal tract include migraine headaches, constipation, high cholesterol, diabetes, autoimmune diseases, irritable bowel syndrome (IBS), irritable bowel disease, sepsis, diarrhea, irregular bowel movements, blood in the stool, Alzheimer's disease, Parkinson's disease, eczema, skin disorders, metabolic syndrome, high relative abundance of antibiotic resistant genes in stool versus the relative abundance in the same genes in a healthy cohort, high blood sugar (A1C) levels, and gastrointestinal bacterial or viral infections. The probiotic formulations of the present disclosure can be administered to prevent, ameliorate, or treat the foregoing conditions or symptoms associated therewith. Briefly, using increased extracellular mannitol and modulated BBB activity the probiotic formulations can produce a decrease in microglia-mediated immune response and decreased α-synuclein aggregation.

In one embodiment, the administered formulation is a probiotic formulation comprising a mixture of viable microorganisms of the species *Pediococcus acidilactici* and viable microorganisms of at least one of *Leuconostoc mesenteroides*, including, in one embodiment, *Leuconostoc mesenteroides* ssp *mesenteroides*, and *Lactobacillus reuteri*.

In one embodiment, the probiotic formulation can further include a viable microorganism independently selected from at least one, at least two, at least three, at least four, or all five of *Lactobacillus paracasei, Lactobacillus plantarum, Bifidobacterium bifidum Bifidobacterium longum* and *Bacillus subtilis*.

In one embodiment, the administered probiotic formulation further comprises a viable microorganism independently selected from at least one, at least two, at least three, at least four, at least five, at least six, at least seven, at least eight, at least nine, at least ten, at least eleven, at least twelve, at least thirteen, at least fourteen, at least fifteen, at least sixteen, or all of the microbial species from the group consisting of *Leuconostoc pseudomesenteroides Leuconostoc sanfrancensis, Leuconostoc amelibiosum, Oenococcus oeni, Lactococcus lactis, Lactococcus intermedius, Lactococcus brevis, Lactococcus buchneri* B-1860, *Lactococcus cellobiosus, Lactococcus fermentum, Lactococcus intermedis, Lactococcus citrovorum, Lactococcus mesenteroides* subsp. *dextranicum, Lactococcus paramesenteroides, Rhodobacter sphaeroides, Pseudomonas fluorescens*, and *Gluconobacter suboxydans*.

In one embodiment, the *Leuconostoc amelibiosum* species is a *Leuconostoc amelibiosum* B-742 strain.

In one embodiment, the *Lactococcus intermedius* species is a *Lactococcus intermedius* NRRL B-3693 strain.

In one embodiment, the *Lactococcus buchneri* species is a *Lactococcus buchneri* B-1860 strain.

In one embodiment, the *Lactococcus cellobioses* species is a *Lactococcus cellobiosus* B-1840 strain.

In one embodiment, the *Lactococcus citrovorum* species is a *Lactococcus citrovorum* B-1147 strain.

In one embodiment, the *Lactococcus mesenteroides* subsp. *dextranicum* species is a *Lactococcus mesenteroides* subsp. *dextranicum* B-1120 strain.

In one embodiment, the *Lactococcus paramesenteroides* species is a *Lactococcus paramesenteroides* B-3471 strain.

In one embodiment, the *Lactococcus lactis* species is a strain selected from the group consisting of *Lactococcus lactis* strain F17851, *Lactococcus lactis* strain F110089 ldh mutant, *Lactococcus lactis* strain F19630 double mutant, and *Lactococcus* strain MG1363.

In one embodiment, the administered probiotic formulation further comprises a mixture of viable microorganisms independently selected from at least one, at least two, at least three, at least four, at least five, at least six, at least seven, or at least eight, of the microbial species from the group consisting of *Lactobacillus plantarum, Lactobacillus paracasei, Lactobacillus rhamnosus, Bifidobacterium bifidum, Bifidobacterium longum, Bacillus subtilis, Lactobacillus casei, Lactobacillus helveticus*, and *Bacillus amyloliquefaciens*.

In one embodiment, the *Lactobacillus casei* species is a *Lactobacillus casei* W8 strain.

In one embodiment, the *Lactobacillus helveticus* species is a *Lactobacillus helveticus* R0052. Strain.

In one embodiment, the administered probiotic formulation further comprises a mixture of viable microorganisms comprising *Lactobacillus plantarum, Lactobacillus paracasei, Lactobacillus rhamnosus, Bifidobacterium bifidum, Bifidobacterium longum, Bacillus subtilis, Lactobacillus helveticus, Lactobacillus casei*, and *Bacillus amyloliquefaciens*.

In another aspect, the present disclosure provides, in at least one embodiment, a method of prophylactically administering a therapeutically effective amount of a probiotic formulation comprising a mixture of viable microorganisms of the species *Pediococcus acidilactici* and at least one of *Leuconostoc mesenteroides* and *Lactobacillus reuteri* to a subject in need thereof to thereby increase the production of mannitol in the gastrointestinal tract.

In another aspect, the present disclosure provides, in at least one embodiment, a method of treating a subject suspected to suffer from low production of mannitol in the gastrointestinal tract by:
(i) analyzing a stool sample obtained from the subject with respect to the abundance of genes associated with gastrointestinal mannitol production to thereby diagnose a low mannitol gastrointestinal condition in the subject; and
(ii) orally administering to the subject a therapeutically effective amount of a probiotic formulation comprising a mixture of viable microorganisms of the species *Pediococcus acidilactici* and at least one of *Leuconostoc mesenteroides* ssp *mesenteroides* and *Lactobacillus reuteri*.

Methods and assays for the qualitative and quantitative detection of mannitol in stool are known to those of skill in the art, and include, for example, the methods described by Laker, M. F. and Mount, J. N., 1980. Mannitol estimation in biological fluids by gas-liquid chromatography of trimethylsilyl derivatives. Clinical Chemistry, 26(3), pp. 441-443; Laker, M. F., Bull, H. J. and Menzies, I. S., 1982. Evaluation of mannitol for use as a probe marker of gastrointestinal permeability in man. European Journal of Clinical Investigation, 12(6), pp. 485-491; Saunders, D. R. and Wiggins, H. S., 1981. Conservation of mannitol, lactulose, and raffinose by the human colon. American Journal of Physiology-Gastrointestinal and Liver Physiology, 241(5), pp. G397-G402; and Zhang, Y., Lee, B., Thompson, M., Glass, R., Lee, R. C., Figueroa, D., Gilman, R., Taylor, D. and Stephenson, C., 2000. Lactulose-mannitol intestinal permeability test in children with diarrhea caused by rotavirus and cryptosporidium. Journal of pediatric gastroenterology and nutrition, 31(1), pp. 16-21.

An example method for analyzing the abundance of genes associated with gastrointestinal mannitol production is hereinafter described in Example 3.

In another aspect, the present disclosure provides, in at least one embodiment, a method of treating a subject suspected to suffer from low production of mannitol in the gastrointestinal tract by:
(i) analyzing a urine or blood sample obtained from the subject with respect to the concentration of mannitol to thereby diagnose a low mannitol condition in the subject; and
(ii) orally administering to the subject a therapeutically effective amount of a probiotic formulation comprising a mixture of viable microorganisms of the species *Pediococcus acidilactici* and at least one of *Leuconostoc mesenteroides* ssp *mesenteroides* and *Lactobacillus reuteri*.

Methods and assays for the qualitative and quantitative detection of mannitol in blood or urine are known to those of skill in the art, and include, for example, the methods described by: Lin, W., Paczynski, R. P., Kuppusamy, K., Hsu, C. Y. and Haacke, E. M., 1997. Quantitative measurements of regional cerebral blood volume using MRI in rats: effects of arterial carbon dioxide tension and mannitol. *Magnetic resonance in medicine*, 38(3), pp. 420-428; Miyagi, M., Yokoyama, H. and Hibi, T., 2007. Sugar microanalysis by HPLC with benzoylation: Improvement via introduction of a C-8 cartridge and a high efficiency ODS column. *Journal of Chromatography B*, 854(1-2), pp. 286-29 Bouatra, S., Aziat, F., Mandal, R., Guo, A. C., Wilson, M. R., Knox, C., Bjorndahl, T. C., Krishnamurthy, R., Saleem, F., Liu, P. and Dame, Z. T., 2013. The human urine metabolome. *PloS one*, 8(9), p.e73076; Miki, K.A.Z.U.N.O.R.I., Butler, R., Moore, D. and Davidson, G., 1996. Rapid and simultaneous quantification of rhamnose, mannitol, and lactulose in urine by HPLC for estimating intestinal permeability in pediatric practice. *Clinical chemistry*, 42(1), pp. 71-75; and Camilleri, M., Nadeau, A., Lamsam, J., Linker Nord, S., Ryks, M., Burton, D., Sweetser, S., Zinsmeister, A. R. and Singh, R., 2010. Understanding measurements of intestinal permeability in healthy humans with urine lactulose and mannitol excretion. *Neurogastroenterology & Motility*, 22(1), pp.e15-e26.

It should be noted that included herein are methods that indicate the substantial absence of mannitol in blood or urine, as may be the case when the concentration of mannitol in blood or urine is lower than the detection limit of the mannitol detection assay that is used.

In another aspect, the present disclosure relates to methods of preparing probiotic formulations.

In one aspect, the present disclosure provides, in at least one embodiment, a method of preparing a probiotic formulation, the method comprising:
(i) providing a mixture of viable microorganisms of the species *Pediococcus acidilactici* and at least one of *Leuconostoc mesenteroides* and *Lactobacillus reuteri*; and
(ii) formulating to mixture to form a probiotic formulation.

In at least one embodiment, the mixture of viable microorganisms can be any mixture of microorganisms set forth herein, including, for example, a viable microorganism independently selected from at least one, at least two, at least three, or all four of *Lactobacillus paracasei, Lactobacillus plantarum, Bifidobacterium bifidum* and *Bifidobacterium longum*.

In another aspect, the disclosure relates to uses of the probiotic formulations of the present disclosure.

Thus in one aspect, the present disclosure further provides, in at least one embodiment, a use of a probiotic formulation comprising a mixture of viable microorganisms of the species *Pediococcus acidilactici* and at least one of *Leuconostoc mesenteroides* and *Lactobacillus reuteri* for treating a subject having a condition characterized by low mannitol production in the gastrointestinal tract.

In one embodiment, the administered probiotic formulation further comprises a viable microorganism independently selected from at least one, at least two, at least three, or all four of *Lactobacillus paracasei, Lactobacillus plantarum, Bifidobacterium bifidum* and *Bifidobacterium longum*.

In one embodiment, the *Leuconostoc mesenteroides* can be *Leuconostoc mesenteroides* ssp *mesenteroides*.

In one aspect, the present disclosure further provides, in at least one embodiment, a probiotic formulation comprising a mixture of viable microorganisms of the species *Pediococcus acidilactici* and at least one of *Leuconostoc mesenteroides* and *Lactobacillus reuteri* for use in the treatment of a subject having a condition characterized by low mannitol production in the gastrointestinal tract.

In one embodiment, the administered probiotic formulation comprises a viable microorganism independently selected from at least one, at least two, at least three, or all four of *Lactobacillus paracasei, Lactobacillus plantarum, Bifidobacterium bifidum* and *Bifidobacterium longum*.

In one embodiment, the *Leuconostoc mesenteroides* can be *Leuconostoc mesenteroides* ssp *mesenteroides*.

In another aspect, the present disclosure provides, in at least one embodiment, a use of a mixture of viable microorganisms of the species *Pediococcus acidilactici* and at least one of *Leuconostoc mesenteroides* ssp *mesenteroides* and *Lactobacillus reuteri* to prepare a probiotic formulation.

In one embodiment, further included in the mixture are a viable microorganism independently selected from at least one, at least two, at least three, or all four of *Lactobacillus paracasei, Lactobacillus plantarum, Bifidobacterium bifidum* and *Bifidobacterium longum*.

In one embodiment, the probiotic formulation is a formulation for treatment of a subject having a condition characterized by low mannitol production in the gastrointestinal tract.

Hereinafter are provided examples of specific embodiments of the compositions of the present disclosure and methods of the present disclosure. The examples are provided for illustrative purposes only, and are not intended to limit the scope in any way.

EXAMPLES

Example 1

Method of Obtaining Microorganisms for Use in the Preparation of a Probiotic Formulation The strains used in the Examples described herein were single organism freeze dried cultures. The strains were obtained from the following companies: The BioCollective, BioSource Cultures and Flavors Inc., Pure Cultures, Inc., Danisco and Nutraceutix, Inc., a Probi company.

Example 2

Method of Preparing a Probiotic Formulation

Individual bacterial species were cultured, centrifuged, and freeze-dried to achieve dry powder stocks. The bacterial species used were: *Leuconostoc mesenteroides, Pediococcus acidilactici, Bacillus subtilis, Bifidobacterium bifidum, Bifidobacterium longum, Lactobacillus reuteri, Lactobacillus paracasei, Lactobacillus plantarum*. Plating methodologies were then employed to determine CFU/g of the dry powder stocks. The dry powder stocks were then blended together and mixed with P95 Nutraflora and D-mannitol prebiotics to achieve the targeted CFUs of each organism, 2% D-mannitol (w:w) and 12% P95 Nutraflora (w:w).The resulting blended mixture was then placed in food-grade 1-3 per day capsules for oral administration to a patient. The dose of each capsule was targeted at >25-30 billion cfu/capsule. CFU targets for individual species can range from $1\times10^6$ to $1\times10^{12}$. An example formulation is described in Example 7.

Example 3

Method of Collecting Stool, Analyzing Microbiome Community, Identifying Mannitol-Producing Microbes or Pathogenic Microbes DNA was isolated from fecal material of a patient, having received a daily dose of the probiotic formulation of Example 7 for a period of 12 weeks. A total of 100-300 mg of fecal material was used for extraction using bead beating before extraction with QIAamp DNA stool mini kit. Using the TruSeq library preparation protocol (Illumina Inc. San Diego, USA). individual libraries were sequenced on the Illumina Hiseq 2000platform (100 bp paired end reads with average insert size=180 bp). Paired-end reads are quality trimmed using the nesoni pipeline (github.com/Victorian-Bioinformatics-Consortium/nesoni), with the parameters set at: minimum length=75, quality cutoff=30, adapter trimming=yes and ambiguous bases=0. Taxonomic and functional annotations were assigned to individual metagenomic reads using the MetaPhlan2 and HUMAnN2 pipelines, respectively. The Biopieces (biopieces.org) package was then used to create custom databases for protein coding genes associated with mannitol-producing pathways, using complete microbial genome (bacteria and archaea) sequences downloaded from NCBI (ftp://ftp.ncbi.nlm.nih.gov/genomes/refseq/bacteria; accessed on 2 Aug. 2017). ShortBRED (bitbucket.org/biobakery/shortbred/wild/Home) was then used to create biomarkers for the mannitol-producing genes using Uniprot as reference database (uniprot.org/). Metagenomic datasets were then mapped against these biomarkers using the short bread quantify.py script implemented in the ShortBRED software. Normalized counts for marker genes, expressed in units of reads per kilobase of reference sequence per million sample reads (RPKMs) were then further used to determine the presence or absence of the mannitol production pathway.

Example 4

Figure 3:
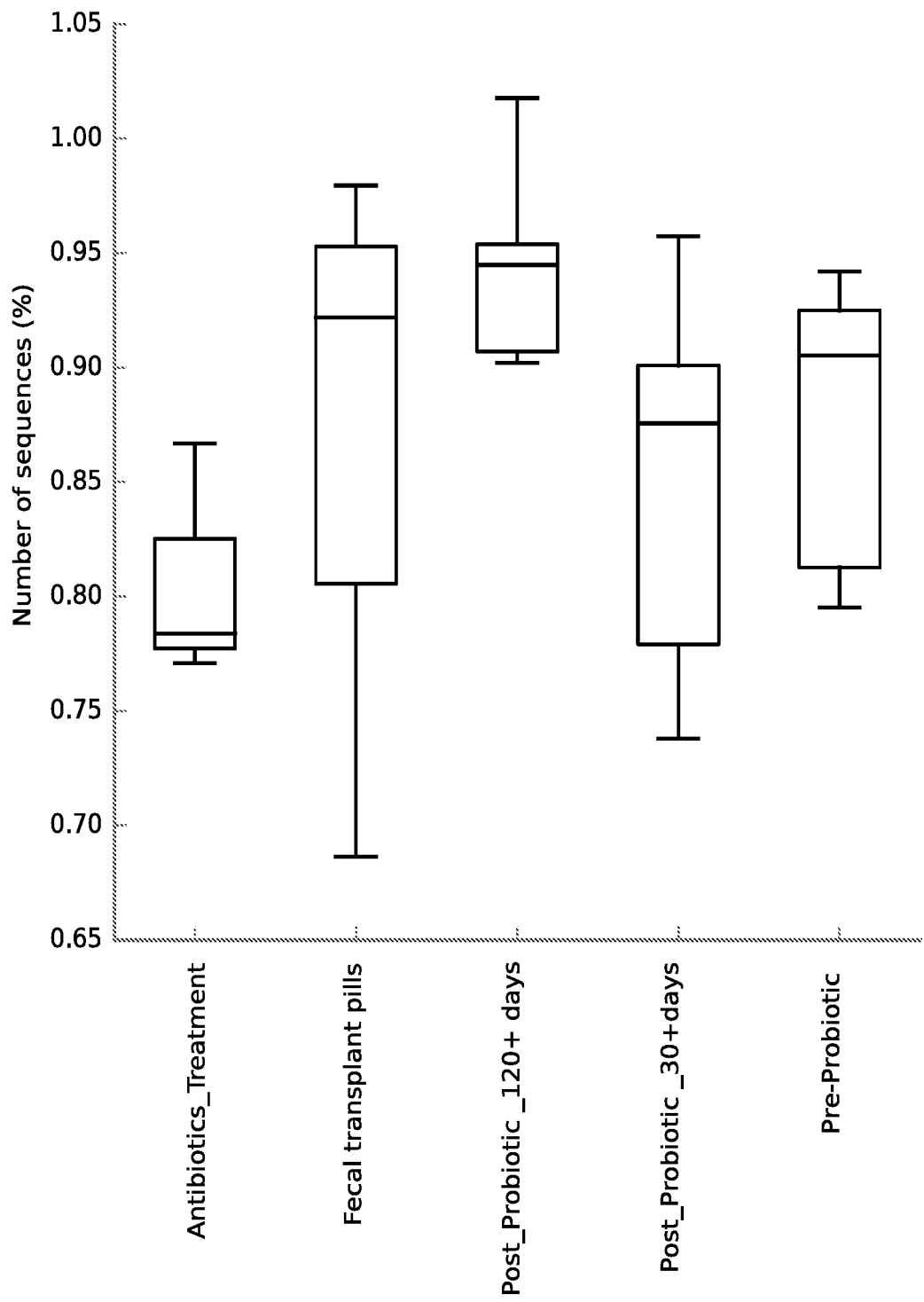
FIG. 3 depicts a graph relating to a metagenomic analysis, notably relative abundance patterns of mannitol producing genes in a recipient patient before, during, and after administration of a probiotic formulation.

Efficacy of Probiotic in Stimulating an Increase in Mannitol Production in the Gastrointestinal System The individual in Example 2 above was monitored for mannitol production in the gastrointestinal system using community genomics methods. As described in Example 3, the stool was collected and sequenced using the Illumina platform. Quality filtered individual metagenome reads were mapped against custom database of mannitol producing genes (constructed using uniprot database). The marker genes responsible for mannitol production/metabolism e.g. mannitol-1-phosphate 5-dehydrogenase (MtlD), mannitol dehydrogenase (MDH), and D-arabinitol 4-dehydrogenase were quantified. MultigroupGenomic analysis of mannitol (ANOVA, multi-test correction=Bonferroni, $p<0.05$) revealed significantly higher abundance of MtlD, MDH, and D-arabinitol 4-dehydrogenase genes across post-probiotic group (after 120 days of probiotic intervention, 1.23%±0.32%) in comparison to pre-probiotic (0.43%±0.02%), fecal microbial transplant (0.85%±0.0032%) and antibiotics period (0.59%±0.01%) .The results are shown in FIG. 3.

Example 5

Figure 4:
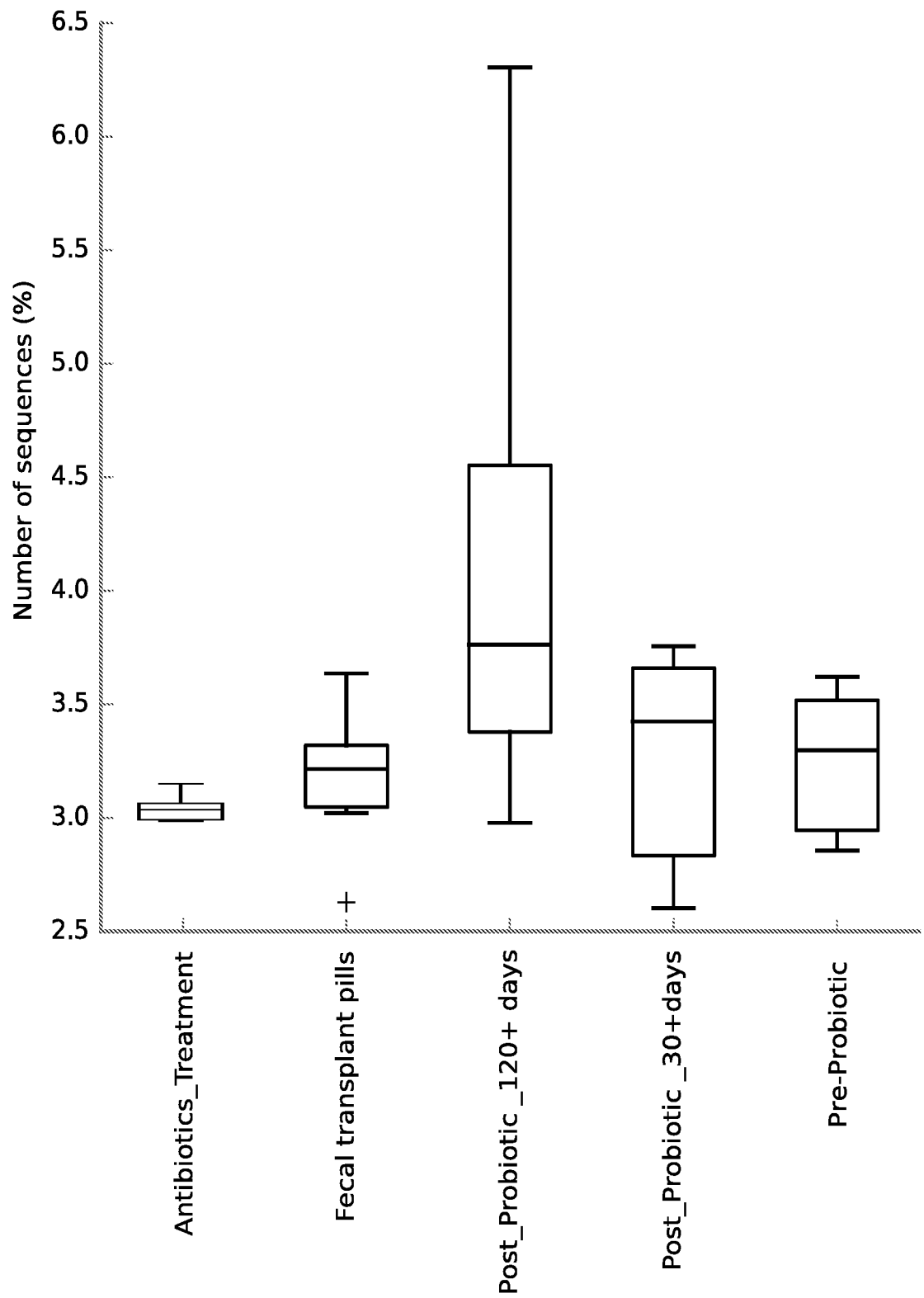
FIG. 4 depicts a graph relating to a metagenomic analysis, notably relative abundance patterns of siderophore genes in a recipient patient microbiome before, during, and after administration of a probiotic.

Efficacy of Probiotic in Stimulating an Increase in Siderophore Content in Gut Microorganisms The individual in Example 2 above was monitored for the relative abundance patterns of genes coding for microbial siderophore in gut microorganisms using assembly based community genomics methods. As described in Example 1, the stool sample was collected and sequenced using the Illumina platform. Quality filtered microbiome reads were assembled into contigs. Protein coding genes (CDS) extracted from metagenome contigs were compared against custom database of microbial siderophores constructed using the hidden markov model (HMM) based methodology. Multigroup analysis (ANOVA, multi-test correction=Bonferroni, $p<0.05$) revealed significantly higher abundance of siderophore genes that are active in the iron siderophore sensor and receptor system including siderophore achromobactin, siderophore aerobactin, siderophore desferrioxamine E, and siderophore enterobactin across the post-probiotic samples (after 120 days of probiotic intervention, 5.23%±0.95%) in comparison to pre-probiotic (4.3%±2.1%), fecal microbial transplant (4.23%±1.0%) and antibiotics period (3.9%±0.23%). The results are shown in FIG. 4.

Example 6

Monitoring Mannitol-Producing Gene Content in Gut Microorganisms

The individual in Example 2 above was monitored for mannitol-producing gene content in gut microorganisms using genomics methods. Individual metagenome reads were mapped on custom made biomarker database (e.g. mannitol dehydrogenase (MDH) enzyme, mannitol-1-phosphate 5-dehydrogenase). Microbiome data (protein coding genes) was used to calculate and compare the relative abundance of marker genes i.e. RPKM (per kilobase per million mapped reads) involved in the bacterial mannitol production e.g. mannitol-1-phosphate 5-dehydrogenase (MtlD) across healthy cohort and individual patients. Furthermore machine learning methods (e.g. Random Forest package in R), were used to validatethe grouping (clustering) patterns of healthy and individual patients.

Example 7

Preparation of a Probiotic Formulation

A probiotic formulation was prepared as described in Table 1, following the methods further described in Examples 1 and 2.

TABLE 1

Probiotic Formulation

| Ingredient | Target cfu/gram | Target cfu/capsule |
|---|---|---|
| Lactobacillus plantarum | $4.38 \times 10^9$ | $2.0 \times 10^9$ |
| Pediococcus acidilactici | $4.38 \times 10^9$ | $2.0 \times 10^9$ |
| Leuconostoc mesenteroides ssp mesenteroides | $4.38 \times 10^9$ | $2.0 \times 10^9$ |
| Lactobacillus reuteri | $1.32 \times 10^{10}$ | $6.01 \times 10^9$ |
| Bifidobacterium bifidum | $4.38 \times 10^9$ | $2.0 \times 10^9$ |
| Lactobacillus paracasei | $4.38 \times 10^9$ | $2.0 \times 10^9$ |
| Bifidobacterium longum | $4.38 \times 10^9$ | $2.0 \times 10^9$ |
| Bacillus subtilis | $6.6 \times 10^8$ | $3.02 \times 10^8$ |
| Fos (P95 Nutraflora ®) | | 50 mgs |
| D-mannitol | | 45 mgs |
| TOTAL | $4.01 \times 10^{10}$ | $1.82 \times 10^{10}$ |

The probiotic formulation is suitable for administration to humans. The characteristics of the formulation are further described in the Examples herein.

Example 8

Administration of Probiotic and Evaluation of Gastrointestinal Mannitol Production, Siderophore Production, Butyrate Production, Glycolysis, and Resistance Genes Probiotic capsules prepared as described in Example 7 were administered to 6 clinical study participants at a dose of 1 capsule per day for a period of 30 days. DNA was isolated from a patient's 100-300 mg of fecal material, as described in Example 3 prior to the 30-day administration period, and again following the 30 day administration period. Shotgun metagenomics, as described by Kaminski J, Gibson M K, Franzosa E A, Segata N, Dantas G, Huttenhower C (2015) High-Specificity Targeted Functional Profiling in Microbial Communities with ShortBRED. PLoS Comput Biol 11(12): e1004557. ShortBRED was used to quantify the relative abundance of genes associated with mannitol production (mannitol-1-phosphate 5-dehydrogenase), siderophore production (Histidine decarboxylase and 3-dehydroshikimate dehydratase), butyrate production (3-hydroxybutyryl-CoA_dehydrogenase and Butyrate kinase), glycolysis (i.e. glucose consumption; Enolase and Pyruvate kinase I), and antibiotic resistance genes in stool samples obtained from the subjects.

Figure 5:
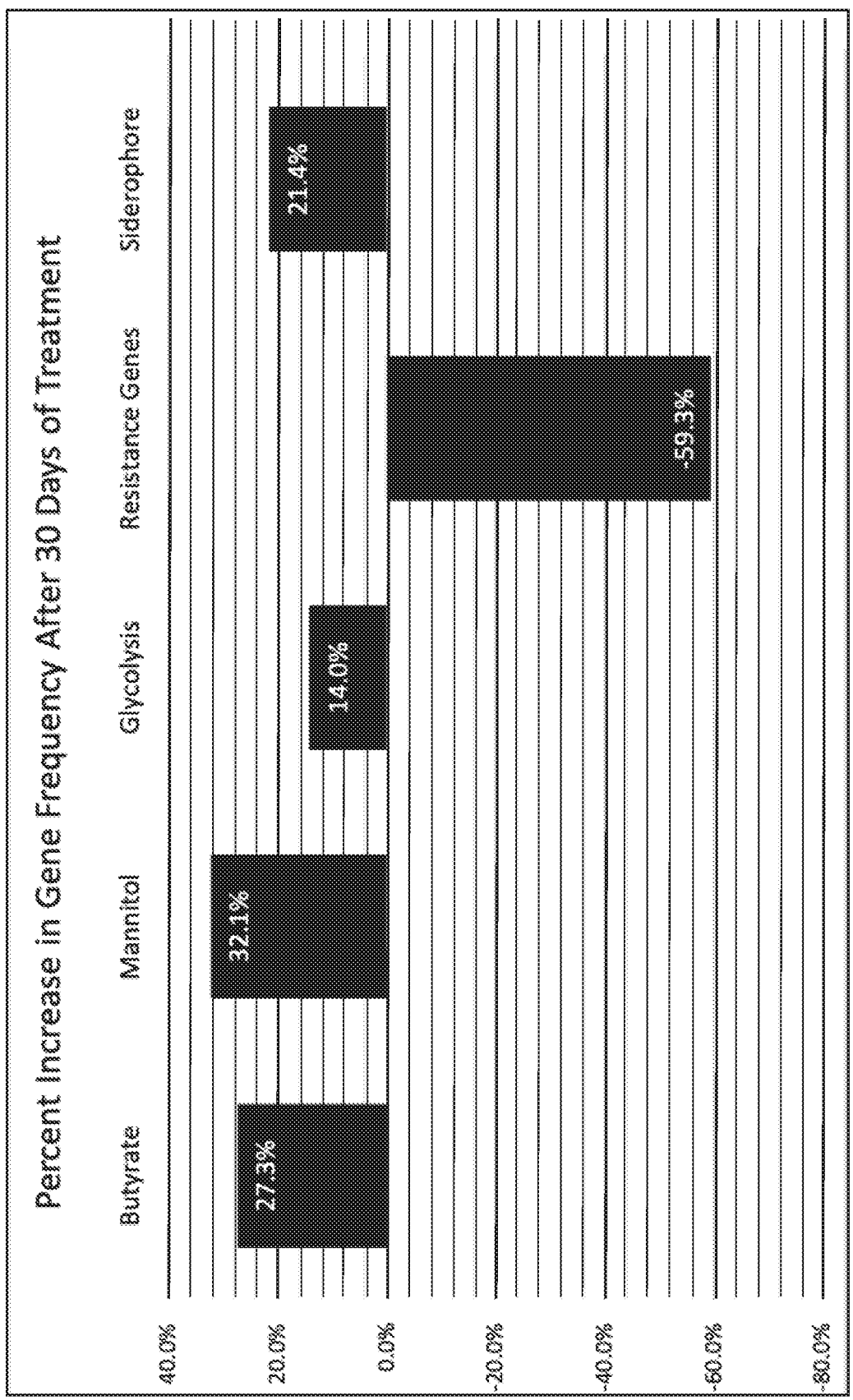
FIG. 5 depicts a bar graph relating to a metagenomic analysis of microbial gastrointestinal genes in human subjects, notably relative abundance of genes relating to butyrate production, mannitol production, glycolysis, resistance, and siderophores.
Figure 6A:
FIGS. 6A-6D depict bar graphs relating to a metagenomic analysis of microbial gastrointestinal genes in human subjects, notably relative abundance of genes associated with mannitol production (FIG. 6A), relative abundance of genes associated with glycolysis and gluconeogenesis (FIG. 6B), relative abundance of genes associated with butyrate biosynthesis (FIG. 6C) and relative abundance of genes associated with antimicrobial resistance genes (FIG. 6D).
Figure 6B:
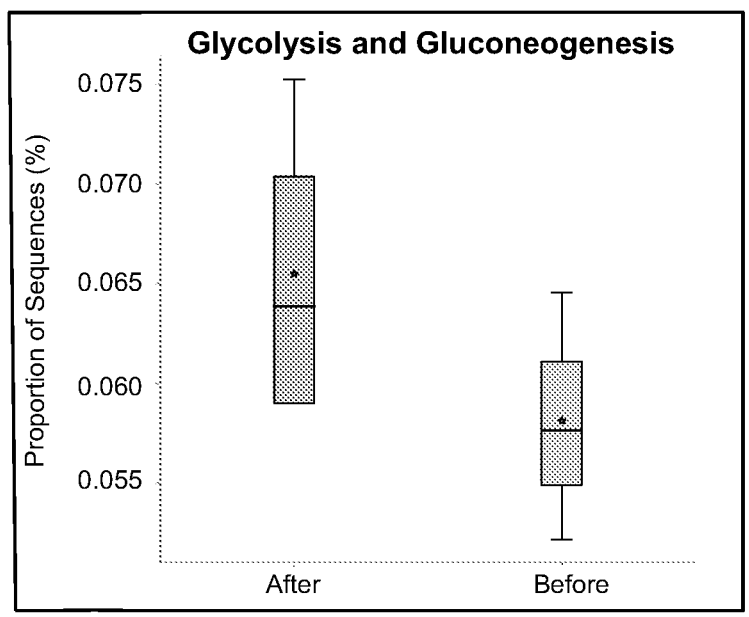
Figure 6C:
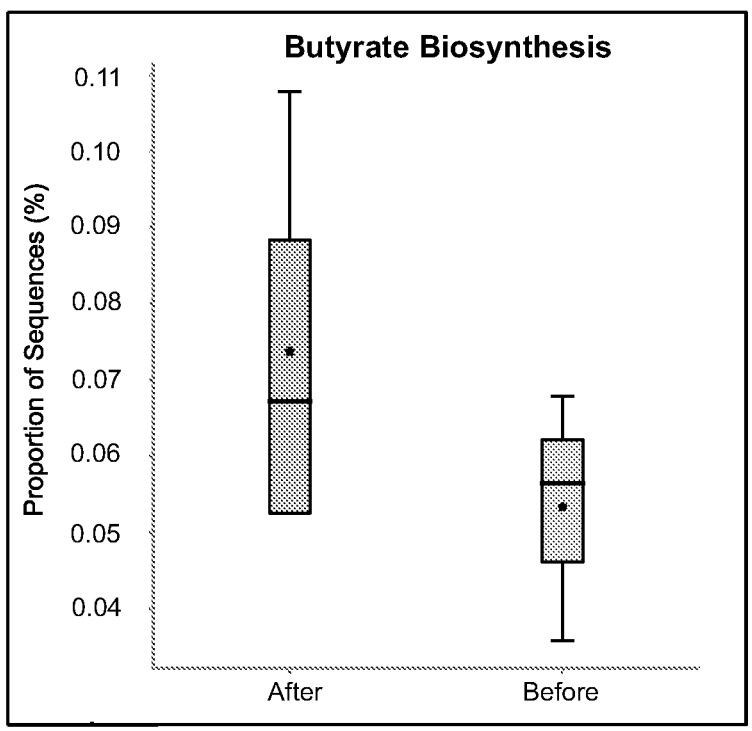
Figure 6D:
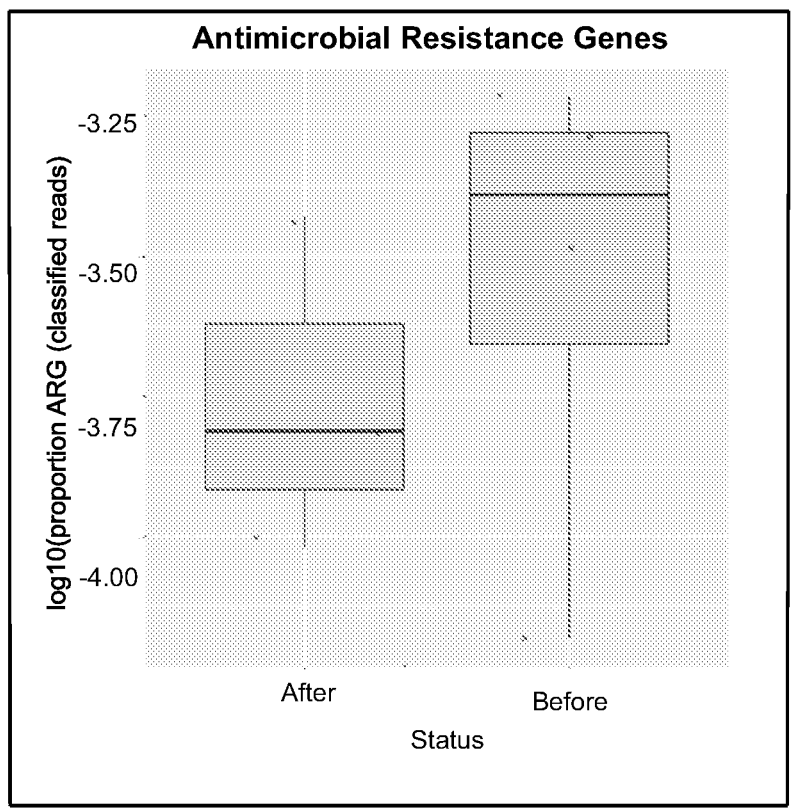

The results are shown in FIG. 5 and FIG. 6. As can be seen in FIG. 5, following the 30 day administration period, the relative abundance of genes associated with mannitol production increased by 32.1%; the relative abundance of genes associated with siderophore production increased by 21.4%, the relative abundance of genes associated with butyrate production increased by 27.3%, the relative abundance of genes associated with glycolysis (i.e. glucose consumption; Enolase and Pyruvate kinase I) increased by 14.0%, and the relative abundance of genes associated with antibiotic resistance genes decreased by 59.3%. Further shown in FIG. 6 are separate results for mannitol production (FIG. 6A), glycolysis (FIG. 6B), butyrate production (FIG. 6C), and antimicrobial. resistance genes (FIG. 6D). The relative abundance of microbial genes was quantified by mapping individual microbial reads on marker genes using Short-BRED) Kaminski J, Gibson M K, Franzosa E A, Segata N, Dantas G, Huttenhower C (2015) High-Specificity Targeted Functional Profiling in Microbial Communities with Short-BRED. PLoS Comput Biol 11(12): e1004557. Briefly, protein coding gene sequences were downloaded for each marker gene using Uniprot database. Each reference gene set (downloaded from Uniprot) was processed for marker set creation using ShortBRED pipeline. BWA aligner was used to map individual microbiome reads on the marker gene sets. Finally, RPKM values were created for each alignment using ShortBRED Example 9

Administration of Probiotic and Evaluation of Gastrointestinal in "Healthy" Biomarker Restoration and Siderophore Production Probiotic capsules prepared as described in Example 7 were administered to a clinical study participant at a dose of 1 capsule per day for a period of 30 days. DNA was isolated from a patient's 100-300 mg of fecal material, as described in Example 3 prior to the 30-day administration period, and again following the 30-day administration period. Shotgun metagenomics, as described by Kaminski J, Gibson M K, Franzosa E A, Segata N, Dantas G, Huttenhower C (2015) High-Specificity Targeted Functional and taxonomic Profiling in Microbial Communities with ShortBRED. PLoS Comput Biol 11(12): e1004557. was used to quantify the relative abundance of genes associated with siderophore production (Histidine decarboxylase and 3-dehydroshikimate dehydratase) in stool samples obtained from the subject.

Figure 10:
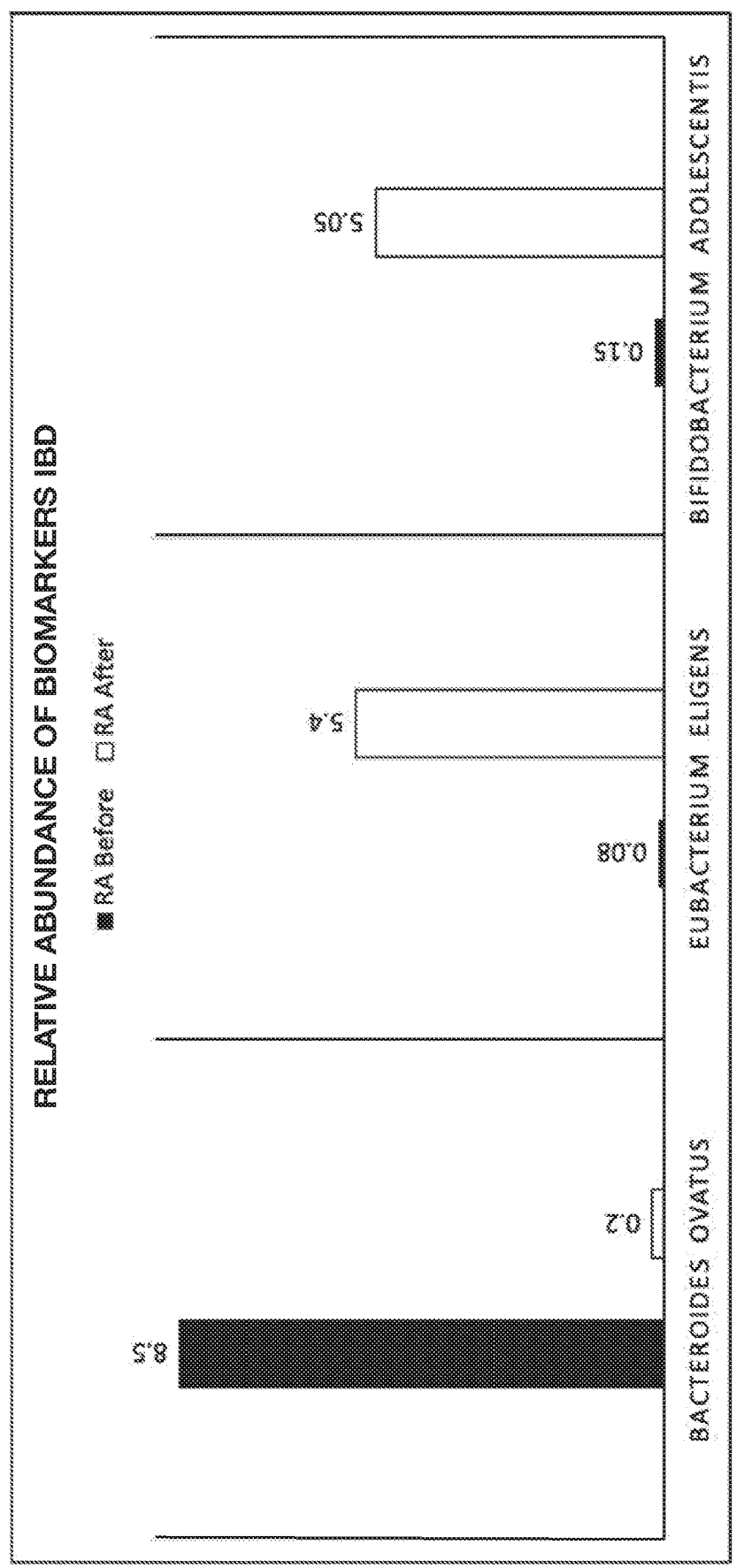
FIG. 10 depicts a bar graph showing the relative abundance of certain biomarkers pre- and post treatment with a probiotic formulation.
Figure 11:
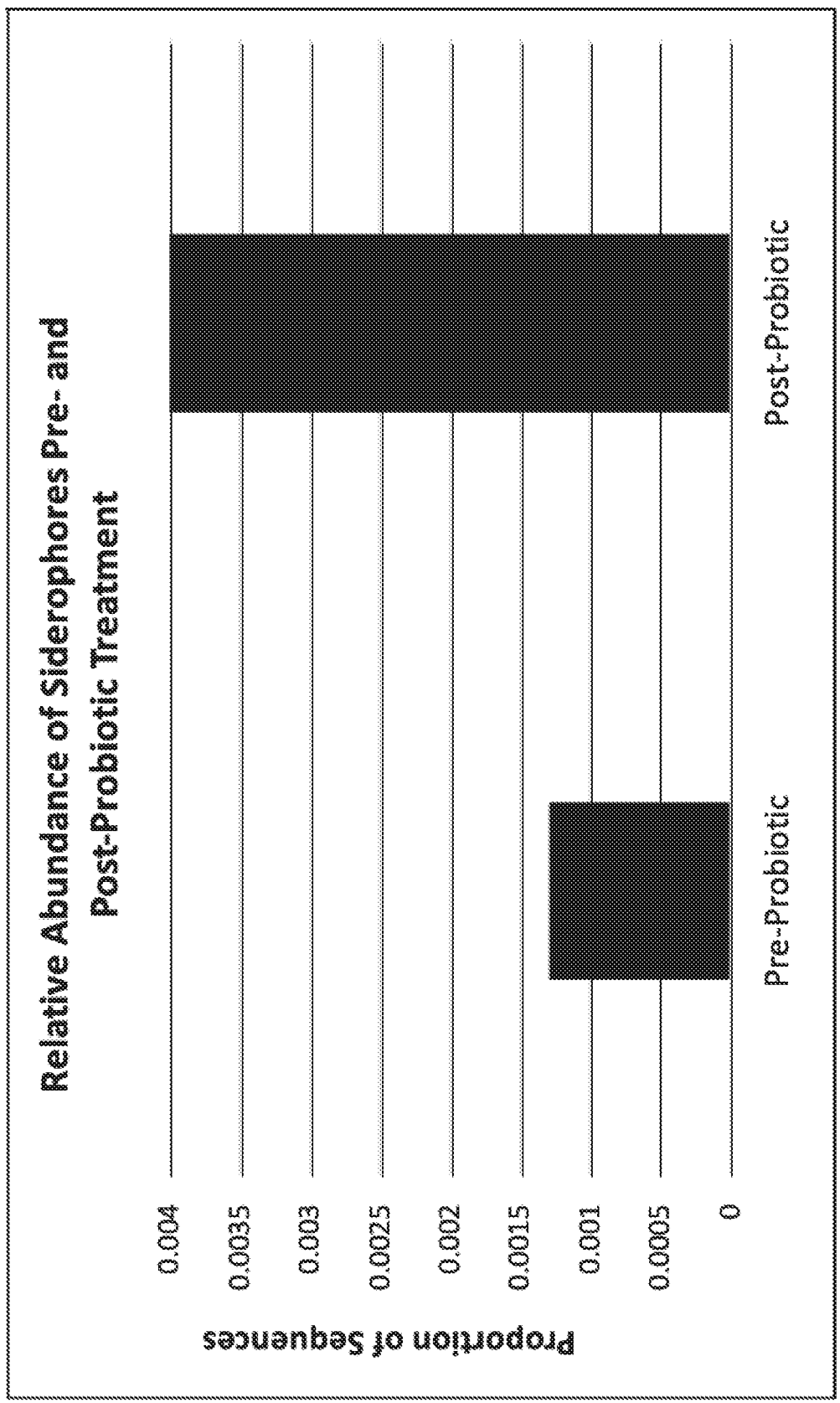
FIG. 11 depicts a bar graph showing the relative abundance of siderophores pre- and post treatment with a probiotic formulation.

The results are shown in FIG. 10 and FIG. 11. As can be seen in FIG. 10, the relative abundance of *Bacteroides ovatus*, a biomarker associated with inflammatory bowel disease and ulcerative colitis (Lucke, K., Miehlke, S., Jacobs, E. and Schuppler, M., 2006. Prevalence of Bacteroides and Prevotella spp. in ulcerative colitis. Journal of medical microbiology, 55(5), pp. 617-624; Guarner, F. and Malagelada, J. R., 2003. Gut flora in health and disease. The Lancet, 361(9356), pp. 512-519; Guarner, F. and Malagelada, J. R., 2003. Gut flora in health and disease. The Lancet, 361(9356), pp. 512-519; and Flint, H. J., Scott, K. P., Louis, P. and Duncan, S. H., 2012. The role of the gut microbiota in nutrition and health. Nature reviews Gastroenterology & hepatology, 9(10), p. 577) decreases significantly. Concurrently, the biomarkers associated with "healthy" adult gut (*Eubacterium elignes* and *Bifidobacterium adolescentis*) increase significantly.

Following the 30-day administration period, the proportion of genes associated with siderophore production increased from 0.13% prior to administration of probiotic to 0.35% after 30 days of treatment as per Example 7. This represented almost a threefold increase. It has been shown that bifidobacteria produce siderophores, which chelates iron thus reducing neutrophil-mediated inflammation and sequester iron from *Bacteroides* spp (Ellermann, M. and Arthur, J. C., 2017. Siderophore-mediated iron acquisition and modulation of host-bacterial interactions. *Free Radical Biology and Medicine*, 105, pp. 68-78).

The relative abundance of microbial genes was quantified by mapping individual microbial reads on marker genes using ShortBRED (Kaminski J, Gibson M K, Franzosa E A, Segata N, Dantas G, Huttenhower C (2015) High-Specificity Targeted Functional Profiling in Microbial Communities with ShortBRED. PLoS Comput Biol 11(12): e1004557. Briefly, protein coding gene sequences were downloaded for each marker gene using Uniprot database. Each reference gene set (downloaded from Uniprot) was processed for marker set creation using ShortBRED pipeline. BWA aligner was used to map individual microbiome reads on the marker gene sets. Finally, RPKM values were created for each alignment using ShortBRED Example 10

Identification of Bacterial Species Involved in Mannitol Production

Figure 7:
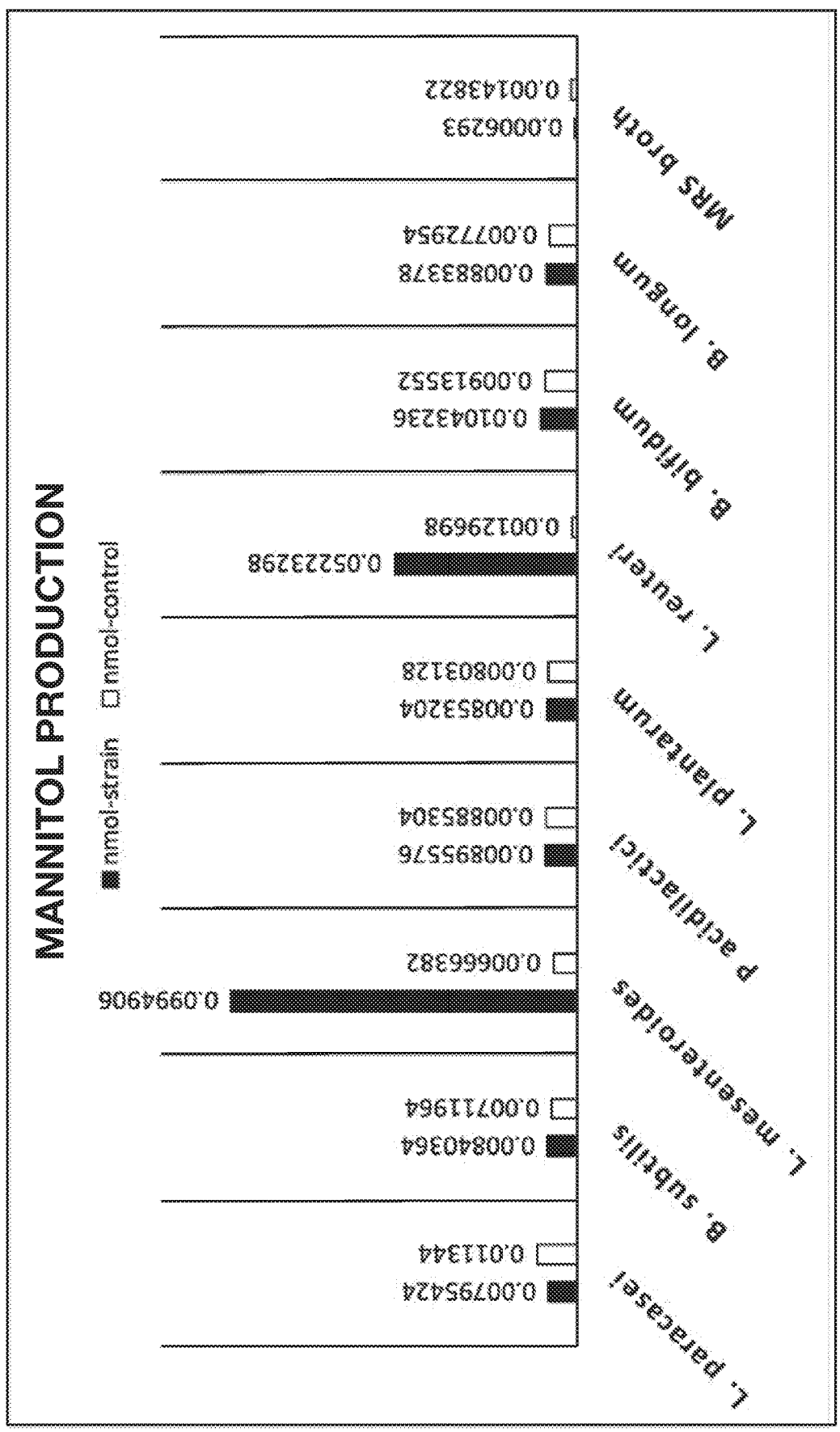
FIG. 7 depicts a bar graph relating to the production of mannitol by each of the denoted microbial species grown in a glucose containing growth medium.

Each of the individual bacterial species constituting the probiotic formulation described in Example 7 was grown separately on a MRS medium for a total of 24 hrs, and the amount of free mannitol was measured using a D-Mannitol colorimetric assay kit (BioVision, Milipitas, CA). The results are shown in FIG. 7. As can be seen in FIG. 7, *Leuconostoc mesenteroides* and *Lactobacillus reuteri* are the primary species producing substantive amounts of D-mannitol, ranging from 0.05 to 0.1 nmol, following 24 hours of growth (darker colored bars). Lighter colored bars represent amounts prior to 24 hours of growth.

Example 11

Identification of Bacterial Species Involved in Glucose Consumption

Figure 8:
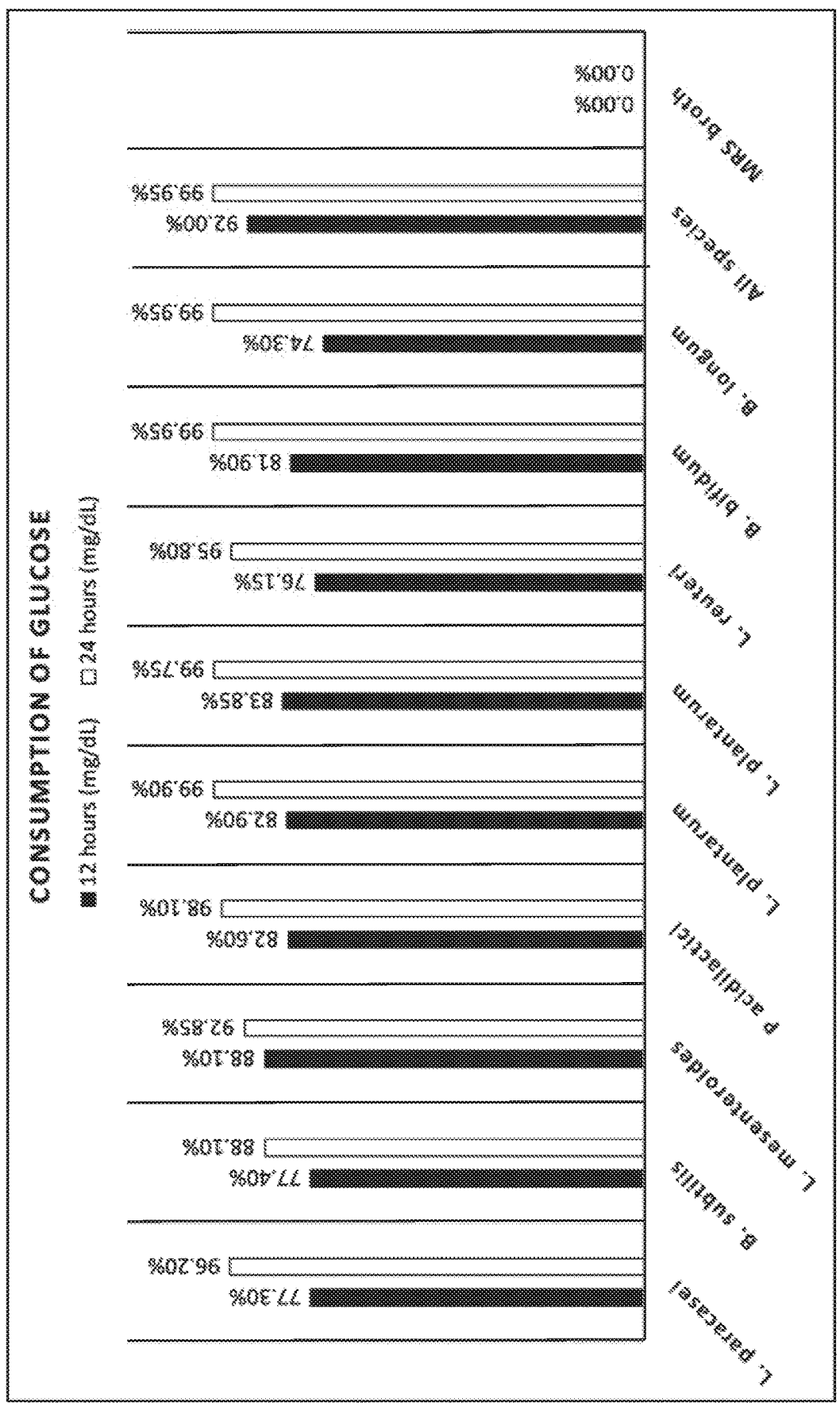
FIG. 8 depicts a bar graph relating to the consumption of glucose by each of the denoted microbial species grown in a glucose containing growth medium.

Each of the individual bacterial species constituting the probiotic formulation described in Example 7 was grown separately on a MRS medium, including 2,000 mg/dl glucose, for a total of 24 hrs, and the amount of glucose was measured using a glucometer, (nextONE). The results are shown in FIG. 8. As can be seen in FIG. 8, all species consume substantial quantities of glucose following 12 hrs (at least 74% of the total amount of glucose) and 24 hrs (at least 88% of the total amount of glucose) of growth, consistent with glycolytic activity during growth. It can also be seen in the results of FIG. 8 that the probiotic formulation is more efficient in consuming glucose than the individual component bacteria. It is noted that glycolysis yields the metabolite fructose-6-phosphate (6FP), which in turn can be used as a substrate to form mannitol. Mannitol can be used by microbial gastrointestinal species as a carbon source.

Example 12

Identification of Bacterial Species Involved in pH Control

Each of the individual bacterial species constituting the probiotic formulation described in Example 7 was evaluated separately in an in silico model based on the composition of the MRS medium, for a total of 24 hrs, using a COBRA (COnstraint-Based Reconstruction and Analysis) metabolic models (Bordbar A., Monk J. M., King Z. A., Palsson B. O. Constraint-based models predict metabolic and associated cellular functions. Nat. Rev. Genet. 2014; 15:107-120). The predicted pH the medium was then determined.

Figure 9:
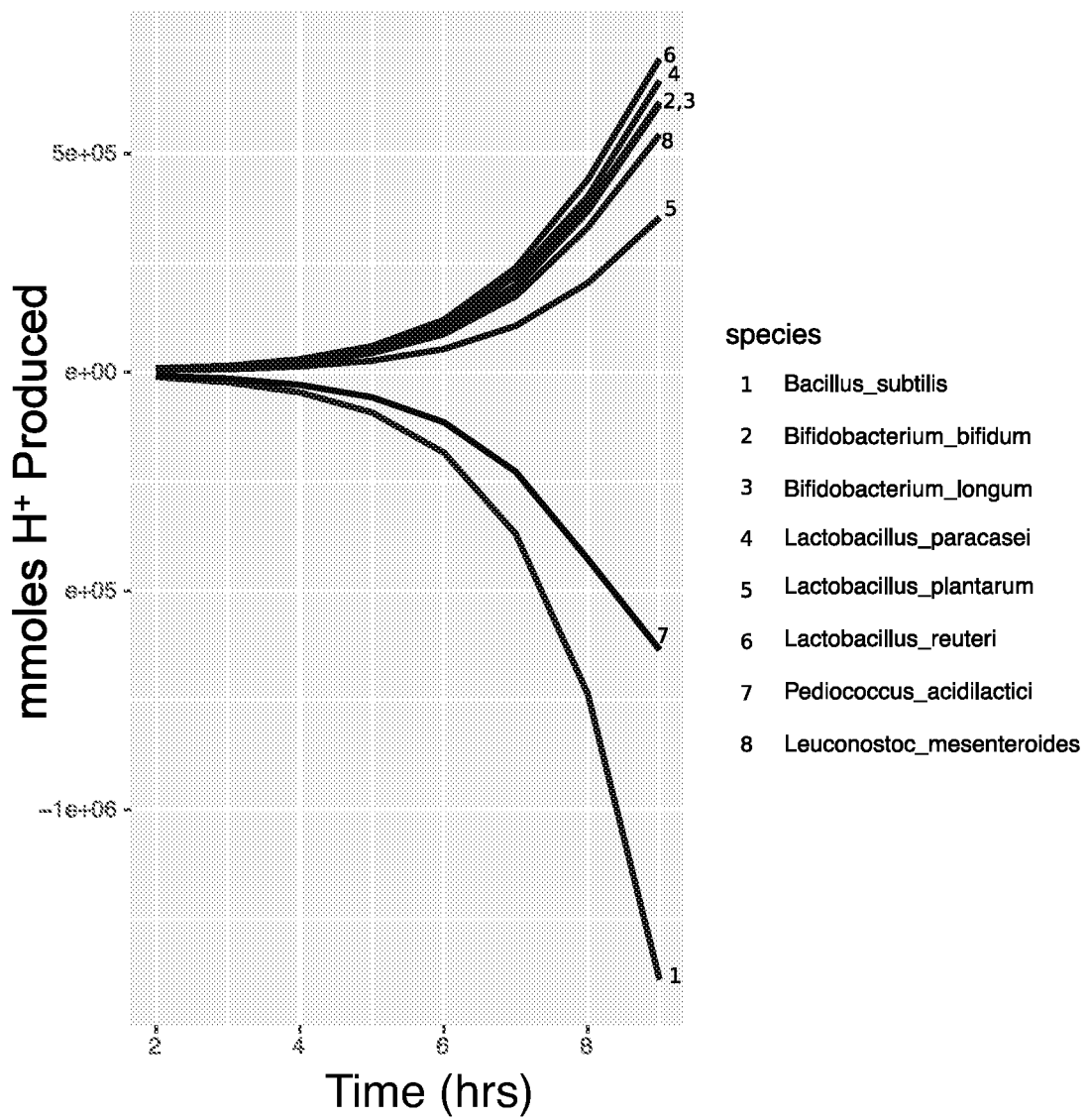
FIG. 9 depicts a graph showing hydrogen ion production by each of the denoted microbial species grown in a glucose containing growth medium.

The results are shown in FIG. 9. As can be seen in FIG. 9, two species, namely *Pediococcus acidilactici* and *Bacillus subtilis* are able to reduce the concentration of hydrogen ions by using the hydrogen ions in metabolic processes. This resulted is more alkaline conditions approximating that of the normal human gut (pH 5.6-7.2). Growth of all other species results in an increase in hydrogen ion production and hence a lowering of the pH. It is noted that prevention of acidification is beneficial since in instances wherein the pH of the medium becomes too low, bacterial growth and metabolic activity, including the production of mannitol by mannitol producing species will be inhibited. Published research indicates that alpha synuclein aggregation is pH dependent and alpha synuclein aggregates faster at low pH. Therefore, the ability to increase the pH should also reduce the speed of aggregation of alpha synuclein.

Example 13

Identification of Bacterial Species Involved in Bacteriocin Production, Butyrate Production and Siderophore Production The literature regarding each of the species of microorganisms included in the formulation of Example 7 was evaluated with respect to the ability to produce bacteriocins, butyrate and siderophore production. It was found that (i) siderophores can be produced by *Pediococcus acidilactici; Lactobacillus plantarum; Bifidobacterium bifidum; Bifidobacterium longum* and *Bacillus subtilis*; (ii) bacteriocin genes can be produced by *Pediococcus acidilactici; Lactobacillus paracasei; Lactobacillus plantarum; Lactobacillus reuteri* and *Bacillus subtilis*; and (iii) butyrate can be produced by *Leuconostoc mesenteroides, Pediococcus acidilactici; Lactobacillus plantarum; Bifidobacterium bifidum; Bifidobacterium longum* and *Bifidobacterium longum*.

Example 14

Identification of Bacterial Species Involved in Mannitol Production, Siderophore Production, pH Control, Glucose Utilization, and Bacteriocin Production The results obtained as described in Examples 9 to 13 are summarized in Table 2 below.

TABLE 2

Gastrointestinal parameters modulated by bacterial species

| Strain/Parameter | Mannitol Prod. [1] | Siderophore Production (Fe+++) | pH Control | Glucose Util. [2] | Bacteriocin genes | Butyrate Prod. |
|---|---|---|---|---|---|---|
| Leuconostoc mesenteroides | X[3] | | | X | | X[4] |
| Pediococcus acidilactici | | X[5] | X | X[6] | X | X[7] |
| Lactobacillus paracasei | | | | X | X[8] | |
| Lactobacillus plantarum | | X[9] | | X | X[10] | X[11] |

TABLE 2-continued

Gastrointestinal parameters modulated by bacterial species

| Strain/Parameter | Mannitol Prod.[1] | Siderophore Production (Fe+++) | pH Control | Glucose Util.[2] | Bacteriocin genes | Butyrate Prod. |
|---|---|---|---|---|---|---|
| Lactobacillus reuteri | X[12] | | | X | X[13] | |
| Bifidobacterium bifidum | | X[14] | | X | | X[15] |
| Bifidobacterium longum | | X[16] | | X | | X[17] |
| Bacillus subtilis | | X[18] | X | X | X[19] | |

[1] Wisselink, H. W., Weusthuis, R. A., Eggink, G., Hugenholtz, J. and Grobben, G. J., 2002. Mannitol production by lactic acid bacteria: a review. International Dairy Journal, 12(2-3), pp. 151-161.
[2] Salvetti, E., Fondi, M., Fani, R., Torriani, S. and Felis, G. E., 2013. Evolution of lactic acid bacteria in the order Lactobacillales as depicted by analysis of glycolysis and pentose phosphate pathways. Systematic and applied microbiology, 36(5), pp. 291-305; Gunsalus, I. C. and Shuster, C. W., 1961. Energy-yielding metabolism in bacteria. In Metabolism (pp. 1-58).
[3] Yun, J. W. and Kim, D. H., 1998. A comparative study of mannitol production by two lactic acid bacteria. Journal of fermentation and bioengineering, 85(2), pp. 203-208.
[4] Yun, J. W. and Kim, D. H., 1998. A comparative study of mannitol production by two lactic acid bacteria. Journal of fermentation and bioengineering, 85(2), pp. 203-208.
[5] Soomro, A. H., Masud, T. and Anwaar, K., 2002. Role of lactic acid bacteria (LAB) in food preservation and human health-a review. Pakistan Journal of Nutrition, 1(1), pp. 20-24.
[6] Garcia, J. M., Castro, S. M., Casquete, R., Silva, J., Queirós, R., Saraiva, J. A. and Teixeira, P., 2017. Enhancement of bacteriocin production and antimicrobial activity of Pediococcus acidilactici HA-6111-2. Acta Alimentaria, 46(1), pp. 92-99.
[7] Wang, W., Chen, L., Zhou, R., Wang, X., Song, L., Huang, S., Wang, G. and Xia, B., 2013. Increased proportion of Bifidobacterium and the Lactobacillus group and loss of butyrate-producing bacteria in inflammatory bowel disease. Journal of clinical microbiology, pp. JCM-01500.
[8] Miao, J., Guo, H., Ou, Y., Liu, G., Fang, X., Liao, Z., Ke, C., Chen, Y., Zhao, L. and Cao, Y., 2014. Purification and characterization of bacteriocin F1, a novel bacteriocin produced by Lactobacillus paracasei subsp. tolerans FX-6 from Tibetan kefir, a traditional fermented milk from Tibet, China. Food Control, 42, pp. 48-53.
[9] Lamont, J. R., Wilkins, O., Bywater-Ekegärd, M. and Smith, D. L., 2017. From yogurt to yield: Potential applications of lactic acid bacteria in plant production. Soil Biology and Biochemistry, 111, pp. 1-9.
[10] da Silva Sabo, S., Converti, A., Todorov, S. D., Dominguez, J. M. and de Souza Oliveira, R. P., 2015. Effect of inulin on growth and bacteriocin production by Lactobacillus plantarum in stationary and shaken cultures. International Journal of Food Science & Technology, 50(4), pp. 864-870.
[11] Wang, W., Chen, L., Zhou, R., Wang, X., Song, L., Huang, S., Wang, G. and Xia, B., 2013. Increased proportion of Bifidobacterium and the Lactobacillus group and loss of butyrate-producing bacteria in inflammatory bowel disease. Journal of clinical microbiology, pp. JCM-01500; Yoshida, Y., Tsukahara, T. and Ushida, K., 2009. Oral administration of Lactobacillus plantarum Lq80 and Megasphaera elsdenii iNP-001 induces efficient recovery from mucosal atrophy in the small and the large intestines of weaning piglets. Animal science journal, 80(6), pp. 709-715.
[12] Ortiz, M. E., Fornaguera, M. J., Raya, R. R. and Mozzi, F., 2012. Lactobacillus reuteri CRL 1101 highly produces mannitol from sugarcane molasses as carbon source. Applied microbiology and biotechnology, 95(4), pp. 991-999.
[13] Yang, Y., Zhao, X., Le, M. H. A., Zijlstra, R. and Gänzle, M., 2015. Reutericyclin producing Lactobacillus reuteri modulates development of fecal microbiota in weanling pigs. Frontiers in microbiology, 6, p. 762.
[14] O'sullivan, D. J., University of Minnesota, 2004. Isolated bifidobacteria that produce siderophores which inhibit growth of Lactococcus lactis. U.S. Pat. No. 6,746,672.
[15] Kanauchi, O., Fujiyama, Y., Mitsuyama, K., Araki, Y., Ishii, T., Nakamura, T., Hitomi, Y., Agata, K., Saiki, T., Andoh, A. and Toyonaga, A., 1999. Increased growth of Bifidobacterium and Eubacterium by germinated barley foodstuff, accompanied by enhanced butyrate production in healthy volunteers. International journal of molecular medicine, 3(2), pp. 175-184.
[16] Vazquez-Gutierrez, P., Lacroix, C., Jaeggi, T., Zeder, C., Zimmerman, M. B. and Chassard, C., 2015. Bifidobacteria strains isolated from stools of iron deficient infants can efficiently sequester iron. BMC microbiology, 15(1), p. 3.
[17] Falony, G., Vlachou, A., Verbrugghe, K. and De Vuyst, L., 2006. Cross-feeding between Bifidobacterium longum BB536 and acetate-converting, butyrate-producing colon bacteria during growth on oligofructose. Applied and environmental microbiology, 72(12), pp.7835-7841.
[18] Yu, X., Ai, C., Xin, L. and Zhou, G., 2011. The siderophore-producing bacterium, Bacillus subtilis CAS15, has a biocontrol effect on Fusarium wilt and promotes the growth of pepper. European Journal of Soil Biology, 47(2), pp. 138-145.
[19] Khochamit, N., Siripornadulsil, S., Sukon, P. and Siripornadulsil, W., 2015. Antibacterial activity and genotypic-phenotypic characteristics of bacteriocin-producing Bacillus subtilis KKU213: potential as a probiotic strain. Microbiological research, 170, pp. 36-50.

It is noted that a probiotic formulation comprising *Pediococcus acidilactici* and at least one of *Leuconostoc mesenteroides* and *Lactobacillus reuteri* can provide for mannitol production, while at the same time preventing acidification, thus ensuring ongoing bacterial growth and metabolic activity, including the production of mannitol by either *Leuconostoc mesenteroides* and *Lactobacillus reuteri*. The same combination of bacterial species additionally permits siderophore production, butyrate production, and bacteriocin production.

REFERENCES

Ahire, J. J., Mokashe, N. U., Patil, H. J., and Chaudhari, B. L. Antioxidative potential of folate producing probiotic *Lactobacillus helveticus* CD6. *J Food Sci Technol.* 50(1), 26-34, (2013).

Calon, F. and Cicchetti, F. Can we prevent Parkinson's disease with n-3 polyunsaturated fatty acids? *Future Lipidology.* 3(2), 133-137, (2008).

Carvalheiro, F., Moniz, P., Duarte, L. C., Esteves, M. P., and Girio, F. M. Mannitol production by lactic acid bacteria grown in supplemented carob syrup. *J Ind Microbiol Biotechnol.* 38, 221-227, (2011).

Cederlund, A., Gudmundsson, G. H., and Agerberth, B. Antimicrobial peptides important in innate immunity. *FEBS Journal.* 278, 3942-3951, (2011).

Christeller, J. T. Evolutionary mechanisms acting on proteinase inhibitor variability. *FEBS Journal.* 272, 5710-5722, (2005).

Emani, A., Ganjkhanlou, M., Nasari, M. H. F., Zali, A., and Rashidi, L. Pomegranate seed pulp as a novel replacement of dietarycereal grains for kids. *Small Ruminant Research.* 238-245, (2015).

Fubini, P. (ed). Mannitol Chemistry, Uses and Potential Side Effects. Nova Science Publishers, New York, NY. 2013.

Galaverna, G., Dall'Asta, C., Corrradini, R., Dossena, A., and Marchelli, R. Cyclodextrins as selectors for mycotoxin recognition. *World Mycotoxin Journal.* 1(4), 397-406, (2008).

Gupta, R., Gupta, N., and Rathi P. Bacterial lipases: an overview of production, purification and biochemical properties. *Appl Microbiol Biotechnol.* 64, 763-781, (2004).

Habibi-Najafi, M. B. and Lee, B. H. Proline-Specific Peptidases of *Lactobacillus case*; Subspecies. *Journal of Dairy Science.* 77, 385-392, (1994).

Harrison, F., Paul, J., Massey, R., and Buckling, A. Interspecific competition and siderophore-mediated cooperation in *Pseudomonas aeruginosa*. *ISME Journal.* 2, 49-55, 2008.

Kurosawa, K., Hosaka, T., Tamehiro, N., Inaoka, T., and Ochi, K. Improvement of_-Amylase Production by Modulation of Ribosomal Component Protein S12 in *Bacillus subtilis* 168. *Appl and Env Microbiol.* 72(1), 71-77, (2006).

Ledesma-Amaro, R. and Nicaud, J. M. Yarrowia lipolytica as a biotechnological chassis to produce usual and unusual fatty acids. *Progress in Lipid Research.* 61, 40-50, (2016).

Liong, M. T. and Shah, N. P. Production of organic acids from fermentation of mannitol, fructooligosaccharide and inulin by a cholesterol removing Lactobacillus acidophilus strain. *Journal of Applied Microbiology.* 99, 783-793, (2005).

Moradian, F., Khajeh, K., Naderi-Manesh, H., Ahmadvand, R., Sajedi, R. H., and Sadeghizadeh, M. Thiol-Dependent Serine Alkaline Proteases from Bacillus sp. HR-08 and KR-8102. *Applied Biochemistry and Biotechnology.* 134, 77-87, (2006).

Ortiz M. E., Bleckwedel J., Fadda S., Picariello G., Hebert E. M., and Raya R. R., et al. Global Analysis of Mannitol 2-Dehydrogenase in *Lactobacillus reuteri* CRL 1101 during Mannitol Production through Enzymatic, Genetic and Proteomic Approaches. *PLoS ONE* 12(1): e0169441. doi: 10.1371/journal.pone.0169441. (2017).

Park, E. J., Kim, K. H., Abell, G. C. J., Kim, M. S., Roh, S. W., and Bae, J. W. Metagenomic Analysis of the Viral Communities in Fermented Foods. *Appl and Env Microbiol.* 77(4), 1284-1291, (2011).

Phibbs, P. V., McCowen, S. M., Feary, T. W., and Blevins, W. T. Mannitol and Fructose Catabolic Pathways of *Pseudomonas aeruginosa* Carbohydrate-Negative Mutants and Pleiotropic Effects of Certain Enzyme Deficiencies. *Journal of Bacteriology.* 133(2), 717-728, (1978).

Rao, A. B., Tanksale, A. M., Ghatge, M. S., and Deshpande, V. V. Molecular and Biotechnological Aspects of Microbial Proteases. *Microbiology and Molecular Biology Reviews.* 597-635, (1998).

Rose, C., Parker, A., Jefferson, B., and Cartmell, E. The Characterization of Feces and Urine: A Review of the Literature to Inform Advanced Treatment Technology. *Critical Reviews in Environmental Science and Technology.* 45(17), 1827-1879, DOI: 10.1080/10643389.2014.1000761. (2003).

Saha, B., and Racine, F. Biotechnological production of mannitol and its applications. *Appl Microbiol Biotechnol.* 89, 879-891, (2011).

Saha, Badal and K Nakamura, Lawrence. Production of mannitol and lactic acid by fermentation with Lactobacillus intermedius NRRL B-3693. *Biotechnology and Bioengineering.* 82. 864-71. 10.1002/bit. 10638. (2003).

Shaltiel-Karyo, R., Frenkel-Pinter, M., Rockenstein, E., Patrick, C., Levy-Sakin, M., Schiller, A., Egoz-Matia, N., Masliah, E., Segal, D., and Gazzit, E. A Blood-Brain Barrier (BBB) Disrupter Is Also a Potent-Synuclein (-syn) Aggregation Inhibitor: A Novel Dual Mechanism of Mannitol for the Treatment of Parkinson Disease (PD). *J Biological Chemistry.* 288(24), 17579-17588, 2013.

Stone, T. W., Darlington, L. G., and Forrest, C. M. Dependence receptor involvement in subtilisin-induced long-term depression and in long-term potentiation. *Neuroscience* 336, 49-62, (2016).

Wasik A and Antkiewicz-Michaluk L. The mechanism of neuroprotective action of natural compounds, *Pharmacological Reports*, 69(5), p 851-860 (2017).

Wisselink, H. W., Weusthuis, R. A., Eggink, G., Hugenholtz, J., and Grobben, G. J. Mannitol production by lactic acid bacteria: a review. *International Dairy Journal.* 12, 151-161, (2002).

Yang, J. K., Shih, I. L., Tzeng, Y. M., and Wang, S. L., Production and purification of protease from a *Bacillus subtilis* that can deproteinize crustacean wastes. *Enzyme and Microbial Technology.* 26, 406-413, (2000).

Yassour, M., Lim, M. Y., Yun, H. S., Tickle, T. L., Sung, J., Song, Y. M., Lee, K., Franzosa, E. A., Morgan, X. C., Gevers, D., Lander, E. S., Xavier, R. J., Birren, B. W., Ko, G., and Huttenhower, C. Sub-clinical detection of gut microbial biomarkers of obesity and type 2 diabetes. *Genome Medicine.* 8(17), 1-14 (2016).

Yeom, S. J., Ji, J. H., Kim, N. H., Park, C. S., and Oh, D. K. Substrate Specificity of a Mannose-6-Phosphate Isomerase from *Bacillus subtilis* and Its Application in the Production of L-Ribose. *Appl and Env Microbiol.* 75(14), 4705-4710, (2009).

The invention claimed is:

1. A probiotic formulation comprising a mixture of viable microorganisms of the species *Pediococcus acidilactici*, *Leuconostoc mesenteroides*, and *Lactobacillus reuteri*, and a formulary ingredient selected from a binder, a diluent and an excipient, wherein the probiotic formulation increases the abundance of microbial gastrointestinal genes associated with mannitol production in a subject upon administration of the formulation to the subject.

2. The probiotic formulation according to claim 1, wherein the *Leuconostoc mesenteroides* species is *Leuconostoc mesenteroides* spp. *mesenteroides*.

3. The probiotic formulation according to claim 1, wherein the probiotic formulation further comprises one or more viable microorganisms independently selected from at least one, at least two, at least three, at least four, or at least all five, of *Lacotobacillus paracasei, Lacotobacillus plantarum, Bifidobacterium bifidum, Bifidobacterium longum*, and *Bacillus subtilis*.

4. The probiotic formulation according to claim 1, wherein the probiotic formulation further comprises one or more viable microorganisms independently selected from at least one, at least two, at least three, at least four, at least five, at least six, at least seven, at least eight, at least nine, at least ten, at least eleven, at least twelve, at least thirteen, at least fourteen, at least fifteen, at least sixteen, or all seventeen of the microbial species from the group consisting of *Leuconostoc pseudomesenteroides, Leuconostoc sanfrancensis, Leuconostoc amelibiosum, Oenococcus oeni, Lactococcus lactis, Lactococcus intermedius, Lactococcus brevis, Lactococcus buchneri, Lactococcus cellobiosus, Lactococcus fermentum, Lactococcus intermedis, Lactococcus citrovorum, Lactococcus mesenteroides* subsp. *dextranicum, Lactococcus paramesenteroides, Rhodobacter sphaeroides, Pseudomonas fluorescens*, and *Gluconobacter suboxydans*.

5. The probiotic formulation according to claim 1, wherein the probiotic formulation further comprises a mixture of viable microorganisms independently selected from at least one, at least two, at least three, at least four, at least five, at least six, at least seven, at least eight, or at least nine of the microbial species from the group consisting of *Lactobacillus plantarum, Lacotobacillus paracasei, Lacotobacillus rhamnosus, Bifidobacterium bifidum, Bifidobacterium longum, Bacillus subtilis, Lactobacillus helveticus, Lactobacillus casei*, and *Bacillus amyloliquefaciens*.

6. The probiotic formulation according to claim 1, wherein the formulation is dosed to comprise amounts of about 1×10^6 CFU to about 1×10^12 CFU per dose of each *Pediococcus acidilactici* and *Leuconostoc mesenteroides*, or *Lactobacillus reuteri*.

7. The probiotic formulation according to claim 1, wherein the probiotic formulation further comprises a prebiotic.

8. The probiotic formulation according to claim 7, wherein the prebiotic is D-mannitol.

9. The probiotic formulation according to claim 8, wherein the D-mannitol comprises from about 1% (w/w) to about 4% (w/w) of the formulation.

10. The probiotic formulation according to claim 1, wherein the abundance of microbial gastrointestinal genes associated with mannitol production in a subject increases in an amount from about 10%, to about 35% upon administration to the subject of the formulation.

11. The probiotic formulation according to claim 1, wherein the probiotic formulation further increases the abundance of microbial gastrointestinal genes associated with siderophore production in the subject.

12. The probiotic formulation according to claim 1, wherein the probiotic formulation further decreases the abundance of microbial gastrointestinal genes associated with bacterial antibiotic resistance in the subject.

13. The probiotic formulation according to claim 1, wherein the probiotic formulation further increases the bacteriocin content produced by gastrointestinal microbes in the subject.

14. The probiotic formulation according to claim 1, wherein the probiotic formulation further increases the abundance of microbial gastrointestinal genes associated with glucose utilization in the subject.

15. A method of treating a condition characterized by low mannitol production in the gastrointestinal tract by orally administering a therapeutically effective amount of a probiotic formulation to a subject in need thereof, the probiotic formulation comprising a mixture of viable microorganisms capable of increasing gastrointestinal mannitol production, wherein the probiotic comprises a mixture of viable microorganisms of the species *Pediococcus acidilactici*, *Leuconostoc mesenteroides*, and *Lactobacillus reuteri*.

16. The method according to claim 15, wherein the method further comprises administering a probiotic formulation comprising a prebiotic.

17. The method according to claim 16, wherein the prebiotic is D-mannitol.

18. The method according to claim 17, wherein the D-mannitol comprises from about 1% (w/w) to about 4% (w/w) of the formulation.

19. A method of treating a subject suspected to suffer from low mannitol production in the gastrointestinal tract by:
   (i) analyzing a stool sample obtained from the subject with respect to the abundance of genes associated with gastrointestinal mannitol production thereby diagnosing a low mannitol gastrointestinal condition in the subject; and
   (ii) orally administering to the subject a therapeutically effective amount of a probiotic formulation comprising a mixture of viable microorganisms of the species *Pediococcus acidilactici, Leuconostoc mesenteroides*, and *Lactobacillus reuteri;*
   or
   (iii) analyzing a urine or blood sample obtained from the subject with respect to the concentration of mannitol thereby diagnosing a low mannitol condition in the subject; and
   (iv) orally administering to the subject a therapeutically effective amount of a probiotic formulation comprising a mixture of viable microorganisms of the species *Pediococcus acidilactici, Leuconostoc mesenteroides*, and *Lactobacillus reuteri*.

* * * * *

UNITED STATES PATENT AND TRADEMARK OFFICE
CERTIFICATE OF CORRECTION

| | |
|---|---|
| PATENT NO. | : 11,850,270 B2 |
| APPLICATION NO. | : 16/770064 |
| DATED | : December 26, 2023 |
| INVENTOR(S) | : Martha Rodgers Carlin et al. |

It is certified that error appears in the above-identified patent and that said Letters Patent is hereby corrected as shown below:

In the Claims

Column 32, In Claim 2, Lines 32-34:
Delete:
"2. The probiotic formulation according to claim 1, wherein the Leuconostoc mesenteroides species is Leuconostoc mesenteroides spp. mesenteroides."
And insert:
-- 2. The probiotic formulation according to claim 1, wherein the Leuconostoc mesenteroides species is Leuconostoc mesenteroides ssp. mesenteroides. --

Signed and Sealed this
Sixth Day of August, 2024

Katherine Kelly Vidal
*Director of the United States Patent and Trademark Office*